United States Patent [19]
Fuchigami et al.

[11] Patent Number: 6,134,948
[45] Date of Patent: Oct. 24, 2000

[54] VENTILATION-CHARACTERISTIC MEASURING APPARATUS

[75] Inventors: Seiji Fuchigami, Tokyo; Kaoru Ichida, Toyohashi, both of Japan

[73] Assignee: Japan Tobacco Inc., Tokyo, Japan

[21] Appl. No.: 09/377,820

[22] Filed: Aug. 20, 1999

Related U.S. Application Data

[63] Continuation of application No. PCT/JP99/01253, Mar. 15, 1999.

[51] Int. Cl.$^7$ .................................................. G01N 15/08
[52] U.S. Cl. ................................................................ 73/38
[58] Field of Search ....................................... 73/38, 1.35

[56] References Cited

U.S. PATENT DOCUMENTS

| | | |
|---|---|---|
| 4,912,964 | 4/1990 | Ohtsuki et al. |
| 5,428,987 | 7/1995 | Rousseau ..................................... 73/38 |

FOREIGN PATENT DOCUMENTS

| | | |
|---|---|---|
| 54-112005 | 8/1979 | Japan . |
| 63-259436 | 10/1988 | Japan . |

*Primary Examiner*—Robert Raevis
*Attorney, Agent, or Firm*—Birch, Stewart, Kolasch & Birch, LLP

[57] ABSTRACT

A ventilation-characteristic measuring apparatus includes a ventilation vessel include of first, second and third cylindrical containers which are airtightly and detachably fitted to one another, and a hoisting and lowering apparatus for hoisting and lowering the third cylindrical container relative to the first and second cylindrical containers. The first, second and third cylindrical containers cooperate with test-piece holding members of test-piece supporting devices to define three airtight chambers. Ventilation characteristics of a cigarette is measured based on a flow rate of air entering into a filter portion of the cigarette disposed in a second airtight chamber and that of air entering into the shredded tobacco of the cigarette disposed in a third airtight chamber as a first airtight chamber on the filter side is evacuated.

15 Claims, 19 Drawing Sheets

VENTILATION-CHARACTERISTIC MEASURING APPARATUS

This is a continuation application of PCT/JP99/01253 filed Mar. 15, 1999 designating the United States for the national phase.

BACKGROUND OF THE INVENTION

1. Technical Field

The present invention relates to a testing apparatus for evaluating qualities of a rod-shaped test piece such as a cigarette, and more particularly to a ventilation-characteristic measuring apparatus which is suited to measure ventilation characteristics of a test piece and which is simple in construction.

2. Related Arts

In order to evaluate qualities of a cigarette, testing is made on various items such as the weight, circumference and length of the cigarette, the hardness of a cigarette portion thereof, and ventilation characteristics of cigarette and filter portions of the cigarette. A typical cigarette testing apparatus comprises an apparatus for measuring ventilation characteristics of a test piece based on a flow rate of air entering into the test piece from the outside of a ventilation vessel when the ventilation vessel is evacuated.

As shown in FIG. 1, a ventilation-characteristic measuring apparatus of this kind comprises a cylindrical container 1 having its upper and lower ends formed with openings for permitting a test piece such as a filter cigarette C to pass therethrough, first, second and third test-piece supporting devices 3a, 3b and 3c, disposed to be spaced from one another in the axial direction of the cylindrical container and coaxially therewith, for elastically holding a cigarette by means of test-piece holding members, and a rotary valve 4 for selectively closing the lower end opening of the cylindrical container 1. In the following explanations, the first, second and third test-piece supporting devices are sometimes collectively denoted by reference numeral 3.

The first, second and third test-piece supporting devices 3a, 3b and 3c are arranged to hold a tip end portion of a filter plug section F of a cigarette C, a boundary portion between the filter section F and a shredded tobacco section T thereof, and a tip end portion of the tobacco section T (i.e., a lower end portion, an intermediate portion, and an upper end portion of the cigarette), respectively. When the lower end opening of the cylindrical container 1 is closed by the rotary valve 4, =the first, second and third test-piece supporting devices 3a, 3b and 3c cooperate with the cylindrical container 1 to define a first, second and third airtight chambers 2a, 2b and 2c.

In FIG. 1, reference numeral 5 denotes a guide through which a cigarette C supplied to the upper end opening of the cylindrical container 1 is introduced into a central part of the third test-piece supporting device 3c, and reference numeral 6 denotes a guide through which the cigarette C is introduced into a central part of the second test-piece supporting device 3b. A stopper 7 is disposed for forward and backward motions at a location below the first test-piece supporting device 3a. The cigarette C is brought in contact at its lower end with the stopper 7 which is moved forward in advance to a location beneath the first test-piece supporting device 3a, whereby the supporting position of the cigarette C by means of the first, second and third test-piece supporting devices 3a, 3b and 3c is determined.

As shown in Japanese provisional patent publication no. 63-259436, for instance, each of the test-piece supporting devices 3, having a peripheral face thereof formed with a threaded groove, is threadedly engaged with a threaded inner peripheral face of a flange-like mounting portion 1a which projects from an inner peripheral face of the cylindrical container 1 radially inwardly of the container, whereby the supporting device is mounted to the cylindrical container. The test-piece supporting device 3 is comprised of a ring-shaped holder 11 shown in FIGS. 2 and 3 and a test-piece holding member 12 made of an elastic material such as rubber and shown in FIGS. 2 and 4. The holder 11 has a ring-like recess 11a formed in a central part of an inner peripheral face of the holder so as to extend along the entire circumference of the inner peripheral face, and two O-ring holding grooves 11b which are formed in the inner peripheral face at locations above and below the recess 11a. The holder 11 is formed with plural communication holes 11d extending radially of the holder and having both ends thereof which are open to an outer peripheral face, formed with a thread 11c, of the holder and the recess 11a, respectively.

The test-piece holding member 12 is comprised of a tubular portion 12a mounted to the inner peripheral face of the holder 11 so as to close an opening face of the recess 11a on the radially inward side, and a flange portion 12c projecting from a central part of the inner peripheral face of the tubular portion 12a in the radially inward direction. A test-piece supporting hole 12b is formed in a central part of the flange portion 12c. As shown in FIG. 2, the test-piece holding member 12 is mounted to the inner peripheral face of the holder 11 through O-rings 13 fitted into the O-ring holding grooves 11b of the holder 11.

The mounting portion 1a, to which the test-piece supporting device 3 is mounted, of the cylindrical container 1 is formed with a suction hole 1b communicating with the communication hole 11d of the holder 11. By sucking, through the suction hole 1b, an air in the recess 11a whose opening face is closed by the tubular portion 12a of the test-piece holding member 12, part of the tubular portion 12a is pulled into the recess 11a and the flange portion 12c is elastically deformed, so that the diameter of the test-piece supporting hole 12b increases. In this condition, a cigarette C is inserted into the test-piece supporting hole 12b. Next, by stopping the suction of air in the recess 11a, the tubular portion 12a, the test-piece supporting hole 12b and the flange portion 12c of the test-piece holding member 12 are restored to their original shapes. As the diameter of the test-piece supporting hole 12b decreases, the cigarette C is supported at its outer peripheral face by the inner peripheral edge, defining the test-piece supporting hole 12b, of the flange portion 12c. At the same time, the flange portion 12c hermetically separates the internal space of the cylindrical container 1 into two spaces defined above and below the flange portion.

In a ventilation characteristic measurement with respect to a filter cigarette C, an amount Vf of air flowing into the second airtight chamber 2b and then entering into the cigarette through its filter plug section F and an amount Vp of air flowing into the third airtight chamber 2c and then entering into the cigarette through its shredded tobacco section T are measured, as the first airtight chamber 2a is evacuated at a predetermined flow rate Vc under a condition that the cigarette C is held in the cylindrical container 1 by means of the test-piece supporting devices 3a, 3b and 3c.

As shown in FIG. 5, a variety of types of cigarettes C is subject to the ventilation characteristic measurement, which are different for the entire cigarette length and for the filter section length. Thus, it is necessary to adjust the three holding positions at which a cigarette C is held by the first, second and third test-piece holding members 3a, 3b and 3c in accordance with the type of a cigarette to be measured, so as to hermetically separate the filter section F and the shredded tobacco section T from each other.

However, the three mounting portions 1a of the cylindrical container 1 are fixedly provided in the aforementioned conventional ventilation-characteristic measuring apparatus. This makes it very difficult to adjust the positions at which the test-piece supporting devices 3a, 3b and 3c are mounted to the cylindrical container 1. If, for example, the holder 11 is thickened, then the position at which the holder is threadedly engaged with the mounting portion 1a of the cylindrical container 1 becomes adjustable to some extent, but no sufficient width for adjustment of the three cigarette holding positions is provided because of constraints in increasing the thickness of the respective holder 11.

The aforesaid test-piece supporting device 3 which is threadedly mounted at its thread 11c to the mounting portion 1a of the cylindrical container 1 is disadvantageous in that much effort is required in mounting the same thereon and dismounting the same therefrom. In addition, the engagement face of the thread 11c at which the test-piece supporting device 3 is mounted on the cylindrical container 1 must be hermetically sealed, in order to control the diameter of the test-piece supporting hole 12b by sucking the air in the recess 11a through the communication hole 11d of the holder 11 and the suction hole 1b formed in the cylindrical container 1 in a condition that these holes are reliably communicated with each other. This necessitates a countermeasure such as the provision of a hermetic seal tape (not shown) for pipe-arrangement use. An operation of providing such a seal tape along the peripheral face of the thread 11c is burdensome. Moreover, the test-piece holding member 12, made of an elastic material such as rubber, entails a deterioration with a elapse of time and must be replaced. Upon replacement of test-piece holding members 12, the test-piece supporting device 3 must be dismounted from the cylindrical container 1. In this manner, the replacement of test-piece holding members 12 is burdensome.

Flow meters of a thermal type primarily employed in measuring air flow rates Vf and Vp are susceptible to affections of measurement circumstances (temperature and humidity), and must be prevented from being contaminated by an air containing dust and oil content. This requires a countermeasure such as a clean laboratory for the flow meters so as to guarantee the measurement accuracy of the flow meters.

Recently, a resistance type flow meter has been employed, and a pressure indicative of a flow rate is detected by means of a minute pressure-difference sensor (pressure sensor), to thereby measure the flow rate of air passing through the resistance type flow meter. However, the minute pressure-difference sensor is extremely high-priced although it is excellent in response characteristic.

SUMMARY OF THE INVENTION

An object of the present invention is to provide a ventilation-characteristic measuring apparatus which permits an easy adjustment of the position at which a rod-shaped test piece is supported, and which is easy to handle and simple in construction.

Another object of the present invention is to provide a ventilation-characteristic measuring apparatus permitting a test-piece supporting device to be mounted to and dismounted from a ventilation vessel with ease.

A further object of the present invention is to provide a ventilation-characteristic measuring apparatus having a test-piece supporting device which is easy to handle and which is easily mounted on and dismounted from a ventilation vessel.

A further object of the present invention is to provide a ventilation-characteristic measuring apparatus having a test-piece supporting device configured to permit a test-piece holding member to be easily mounted to and dismounted from a ring-shaped holder.

Another object of the present invention is to provide a ventilation-characteristic measuring apparatus which accurately measures flow rates of air entering through a filter section F of a filter cigarette and of air entering through a shredded tobacco section thereof, easily calibrates a measured flow rate of air, and is excellent in maintenance performance.

A ventilation-characteristic measuring apparatus according to the present invention comprises a first cylindrical container having an outer end formed with an opening which permits a test piece to pass therethrough and which is selectively hermetically closed, a second cylindrical container disposed coaxially with the first cylindrical container and hermetically detachably fitted to the first cylindrical container, a third cylindrical container having an outer end which is formed with an opening which permits the test piece to pass therethrough and which is disposed coaxially with the first and second cylindrical containers, the third cylindrical container being disposed on a side away from the first cylindrical container with respect to the second cylindrical container in an axial direction of the ventilation-characteristic measuring apparatus and being hermetically detachably fitted to the second cylindrical container, the third cylindrical container cooperating with the first and second cylindrical containers to form a ventilation vessel, a moving apparatus for axially moving the third cylindrical container, and first, second and third test-piece supporting devices, detachably mounted to inner peripheral faces of the first, second and third cylindrical containers, respectively, for holding the test piece.

According to the ventilation-characteristic measuring apparatus of the present invention, the ventilation vessel comprised of the first, second and third cylindrical containers is, as a whole, simple in construction and is assembled and disassembled with ease. More specifically, in order to assemble the ventilation vessel, the second cylindrical container is fitted to the first cylindrical container in a condition that the third cylindrical container is caused to recede with use of the moving apparatus, and then the third cylindrical container is moved and fitted to the second cylindrical container. To disassemble the ventilation vessel, the third cylindrical container is dismounted from the second cylindrical container, and then the second cylindrical container is detached from the first cylindrical container.

By replacing at least one of the first, second and third cylindrical containers by one or more containers which are different in axial dimension therefrom, an axial distance between corresponding ones of the first, second and third cylindrical containers can be changed. Thus, the ventilation-characteristic measuring apparatus of the present invention is suited to carry out a ventilation test in respect of test pieces having different specifications, such as filter cigarettes having filter and shredded tobacco sections which are different in length depending on their specifications.

In the ventilation-characteristic measuring apparatus of the present invention, the first, second and third cylindrical containers may be configured to be disposed in a vertical position, so that the second cylindrical container is fitted to the first cylindrical container from above the first cylindrical container and that the third cylindrical container is fitted to the second cylindrical container from above the latter container. In this case, it is sufficient to fix the first and third cylindrical containers to a base plate and a movable part of a hoisting and lowering apparatus which constitutes the moving apparatus, respectively, without the need of supporting the second cylindrical container.

Preferably, each of the first, second and third cylindrical containers is formed into a circular cylindrical container which is an annulus ring in traverse section, whereby a traverse sectional size of each cylindrical container can be reduced, each container can be machined with ease, and airtightness between corresponding ones of these containers can be improved.

In the ventilation-characteristic measuring apparatus of this invention, preferably, the first, second and third cylindrical containers are configured such that the second cylindrical container is fitted into the first cylindrical container and the third cylindrical container is fitted into the second cylindrical container.

With the just-mentioned preferred arrangement, transverse sectional dimensions of the ventilation vessel comprised of the first, second and third cylindrical containers can be reduced. Further, first and second test-piece supporting devices respectively mounted to the first and second cylindrical containers can be disposed in such a manner that these test-piece supporting devices are close to each other, whereby a ventilation-characteristic measuring apparatus suited to a ventilation test on cigarettes having a filter section which is short in length can be provided.

In the preferred arrangement, preferably, the second cylindrical container has a flange which is adapted to abut against an end face of the first cylindrical container on a side close to the second cylindrical container. The ventilation-characteristic measuring apparatus further includes a spacer which is mounted between the flange and an end face of the first cylindrical container.

With the just-mentioned further preferred arrangement, a positional range within which the second cylindrical container is permitted to be mounted to the first cylindrical container can be expanded by mounting the spacer between the flange of the second cylindrical container and an upper end face of the first cylindrical container. Thus, the axial distance between the first and second test-piece supporting devices can be increased with use of the spacer, without the need of replacing the first or second cylindrical container by one having a different axial dimension. This makes it possible for the ventilation-characteristic measuring apparatus to be suited to the ventilation test on various filter cigarettes which are different in filter length.

Preferably, the ventilation-characteristic measuring apparatus of this invention further comprises a rod-shaped member holder, disposed at a location outside the ventilation vessel, for holding a positioning rod-shaped member in parallel to an axis of the ventilation vessel. The moving apparatus includes a movable member to which the third cylindrical container is mounted, and a guide member movable in unison with the movable member and adapted to abut against one end of the positioning rod-shaped member held by the rod-shaped member holder.

With the just-mentioned preferred arrangement, the third cylindrical container can be easily accurately positioned at an optimum mounting position, by moving the third cylindrical container from a location receding from the second cylindrical container up to a location at which the guide member is brought in contact with the one end of the rod-shaped member held by the rod-shaped member holder.

In the ventilation-characteristic measuring apparatus of this invention, preferably, each of the first, second and third test-piece supporting devices comprises a ring-shaped holder having an inner peripheral face on which a test-piece holding member for detachably holding the test piece is held, and a pair of ring-shaped seal members mounted on an outer peripheral face of the ring-shaped holder at locations on axially opposite sides of this outer peripheral face. The ring-shaped holder is fitted on an inner peripheral face of a corresponding one of the first, second and third cylindrical containers. With the just-mentioned preferred arrangement, the holder which holds the test-piece holding member can be detachably mounted to the cylindrical container with ease, through the seal member, i.e., by utilizing an elastic force produced between the seal member and the cylindrical container.

In the ventilation-characteristic measuring apparatus of this invention, preferably, each of the first, second and third test-piece supporting devices comprises a ring-shaped holder detachably mounted to an inner peripheral face of a corresponding one of the first, second and third cylindrical containers, and a test-piece holding member made of an elastic material and formed with a test-piece supporting hole which permits the test piece to pass therethrough. The ring-shaped holder is formed at its inner peripheral face with a recess extending along the whole circumference thereof and is formed with a communication hole having opposite ends thereof opening to the recess and an outer peripheral face of the ring-shaped holder, respectively. The test-piece holding member comprises a tubular portion mounted to the inner peripheral face of the ring-shaped holder and closing an open face of the recess, and an annular flange radially inwardly projecting from the inner peripheral face of the tubular portion. The annular flange has its inner peripheral edge which defines the test-piece supporting hole. Each of the test-piece supporting devices further includes a pair of ring-shaped seal members which are mounted on opposite axial end sides of the outer peripheral face of the ring-shaped holder, respectively. The pair of ring-shaped seal members provide a seal between the ring-shaped holder and the inner peripheral face of the corresponding one cylindrical container, and form a space, communicating with the communication hole, between the outer peripheral face of the ring-shaped holder and the inner peripheral face of the corresponding one cylindrical container.

With the ventilation-characteristic measuring apparatus having the just-mentioned preferred test-piece supporting device, the ring-shaped holder which holds the test-piece holding member can be detachably mounted to the cylindrical container through the pair of seal members, so that the test-piece supporting device can be easily mounted to and dismounted from the cylindrical container. A test piece can be inserted into the test-piece supporting hole of the flange projecting from the tubular portion of the test-piece holding member in a condition that part of the tubular portion is pulled into the recess of the ring-shaped holder so as to increase the diameter of the test-piece supporting hole, by sucking air in the recess from the outside of the ventilation vessel through the space defined on the side of the outer peripheral face of the holder by means of the pair of seal members and through the communication hole communicating with this space. Then, the test piece can be held by the inner peripheral edge of the flange which defines the test-piece supporting hole by stopping the suction of air so as to decrease the diameter of the test-piece supporting hole to an original diameter. At this time, the open face of the recess of the ring-shaped holder is airtightly closed by the tubular portion of the test-piece holding member and an airtight space is formed on the side of the outer peripheral face of the holder by the pair of seal members. Further, the diameter of the test-piece supporting hole increases and decreases in response to the suction of air performed from the outside and the termination of the suction of air, whereby the support of the test piece by means of the test-piece holding member can be established and released in a stable manner with reliability.

In the ventilation-characteristic measuring apparatus having the just-mentioned preferred test-piece supporting device, preferably, the holder is provided at its outer peripheral face with a position-regulating portion for regulating positions at which the pair of ring-shaped seal members are mounted. With this preferred arrangement, the airtight space on the outer peripheral face of the holder by the pair of seal members can be reliably formed, so that the support of the test piece can be stably securely achieved and released by terminating and by performing the suction of air from the outside.

Preferably, the test-piece holding member is provided at axially opposite ends of the tubular portion with a pair of jaw portions between which the holder is sandwiched, whereby the test-piece holding member is mounted to the holder. More preferably, the holder comprises a pair of pressers fixed to axially opposite faces of the holder, respectively, through the jaw portions of the test-piece holding member mounted to the holder. Preferably, the presser fixed to an axially outer face of the holder is formed into an annular shape and has its inner peripheral edge portion which is formed into a truncated conical face through which the test piece is introduced into the test-piece supporting hole of the test-piece holding member.

With the test-piece holding member having the tubular portion provided with the jaw portions or with both the jaw portions and the pressers, the test piece can be mounted to the holder with reliability. With the test-piece holding member having the presser which has the inner peripheral edge portion thereof formed into a truncated conical face, the test piece is accurately aligned with the test-piece supporting hole.

Preferably, the ventilation-characteristic measuring apparatus of this invention comprises a suction apparatus, connected through a first pipe to a first airtight chamber defined by the ventilation vessel and the first test-piece supporting device, for evacuating the first airtight chamber at a flow rate regulated by a critical nozzle, a first flow meter, disposed in a second pipe connected to a second airtight chamber which is defined by the ventilation vessel and the first and second test-piece supporting devices and which opens to the atmospheric air, for generating a pressure corresponding to a flow rate of air entering into the second airtight chamber through the second pipe as the first airtight chamber is evacuated, a second flow meter, disposed in a third pipe which is connected to a third airtight chamber defined by the ventilation vessel and the second and third test-piece supporting devices, for generating a pressure corresponding to a flow rate of air entering the third airtight chamber through the third pipe, a pressure meter, connected to the first and second flow meters through a fourth pipe, for measuring pressures generated in the first and second flow meters, passage changeover valves, disposed in the first, second and third pipes, respectively, for selectively connecting the suction apparatus with the first or second flow meter, and calibration apparatus for calibrating flow rate measuring characteristics of the first and second flow meters based on pressures measured by the pressure meter as the first and second flow meters are evacuated by the suction apparatus.

With the preferred ventilation-characteristic measuring apparatus, in order to carry out the flow rate measurement for evaluating qualities of the test piece, flow rates of air entering into the second and third airtight chambers of the ventilation vessel are measured by the first and second flow meters as the first airtight chamber of the ventilation vessel is evacuated by the suction apparatus which is connected through corresponding ones of the passage changeover valves to the ventilation vessel. In order to make a calibration of the flow rate measuring characteristic of the first or second flow meter, the calibration is carried out based on a pressure which is generated in the flow meter as the air is sucked through the flow meter by the suction apparatus connected through corresponding ones of the passage changeover valves and which is measured by the pressure meter. In this manner, a pipe arrangement required for the flow rate measurement or the calibration can be easily constructed only by switching the passage changeover valves, whereby the flow rate measurement and the calibration can be carried out with use of the apparatus having a simplified construction.

In the preferred version of the ventilation-characteristic measuring apparatus, preferably, each of the first and second flow meters generates a pressure difference between inlet and outlet ports thereof, the pressure difference varying in dependence on the flow rate of air flowing through the flow meter, and the pressure meter is comprised of a pressure difference sensor. The ventilation-characteristic measuring apparatus further comprises first and second pressure-difference pipes extending between the inlet and outlet ports of the first and second flow meters and constituting the fourth pipe, and pressure changeover valves, respectively disposed in the first and second pressure-difference pipes, for selectively connecting the pressure meter to the first or second pressure-difference pipe. With this preferred arrangement, the flow rate measuring characteristics of the first and second flow meters can be rapidly calibrated, and the number of high-priced pressure difference sensors can be decreased to one.

Preferably, the calibration apparatus determines, as a pressure at 100% flow rate, the pressure measured by the pressure meter when the interior of each of the first and second flow meters is evacuated by the suction apparatus, determines, as a pressure at 0% flow rate, the pressure measured by the pressure meter when each of the flow meters is not evacuated by the suction apparatus, determines a calibration line in relation to the pressure and the flow rate in the flow meter, and calibrates the flow rate measuring characteristic in accordance with the calibration line. With this preferred arrangement, the flow rate measuring characteristic can be properly calibrated.

DETAILED DESCRIPTION

With reference to the appended drawings, a cigarette testing apparatus equipped with a ventilation-characteristic measuring apparatus according to an embodiment of the present invention will be explained hereinbelow.

Whole Arrangement

Figure 6:
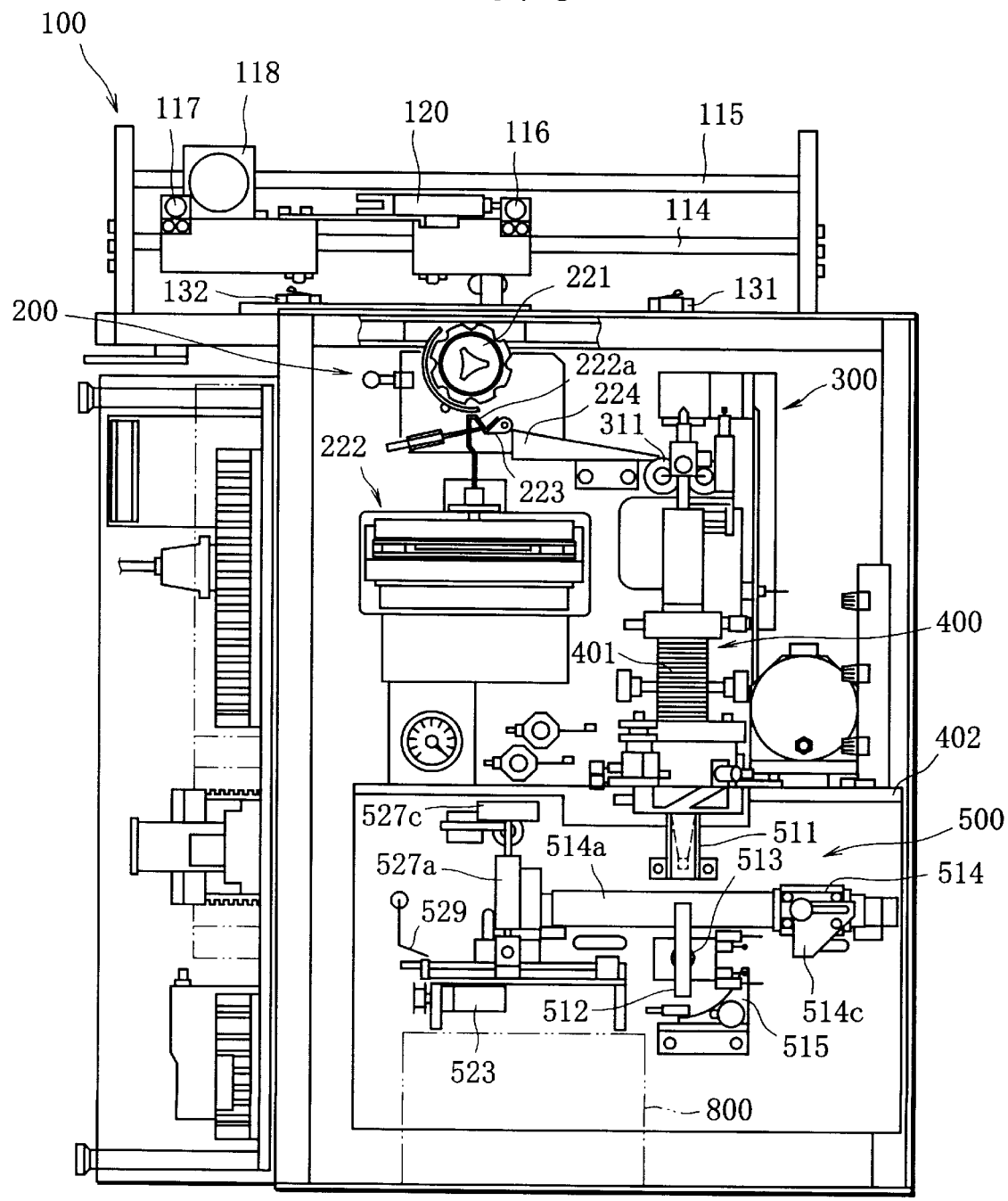
FIG. 6 is a front view showing a primary part of a cigarette testing apparatus equipped with a ventilation-characteristic measuring apparatus according to an embodiment of the present invention.
Figure 22:
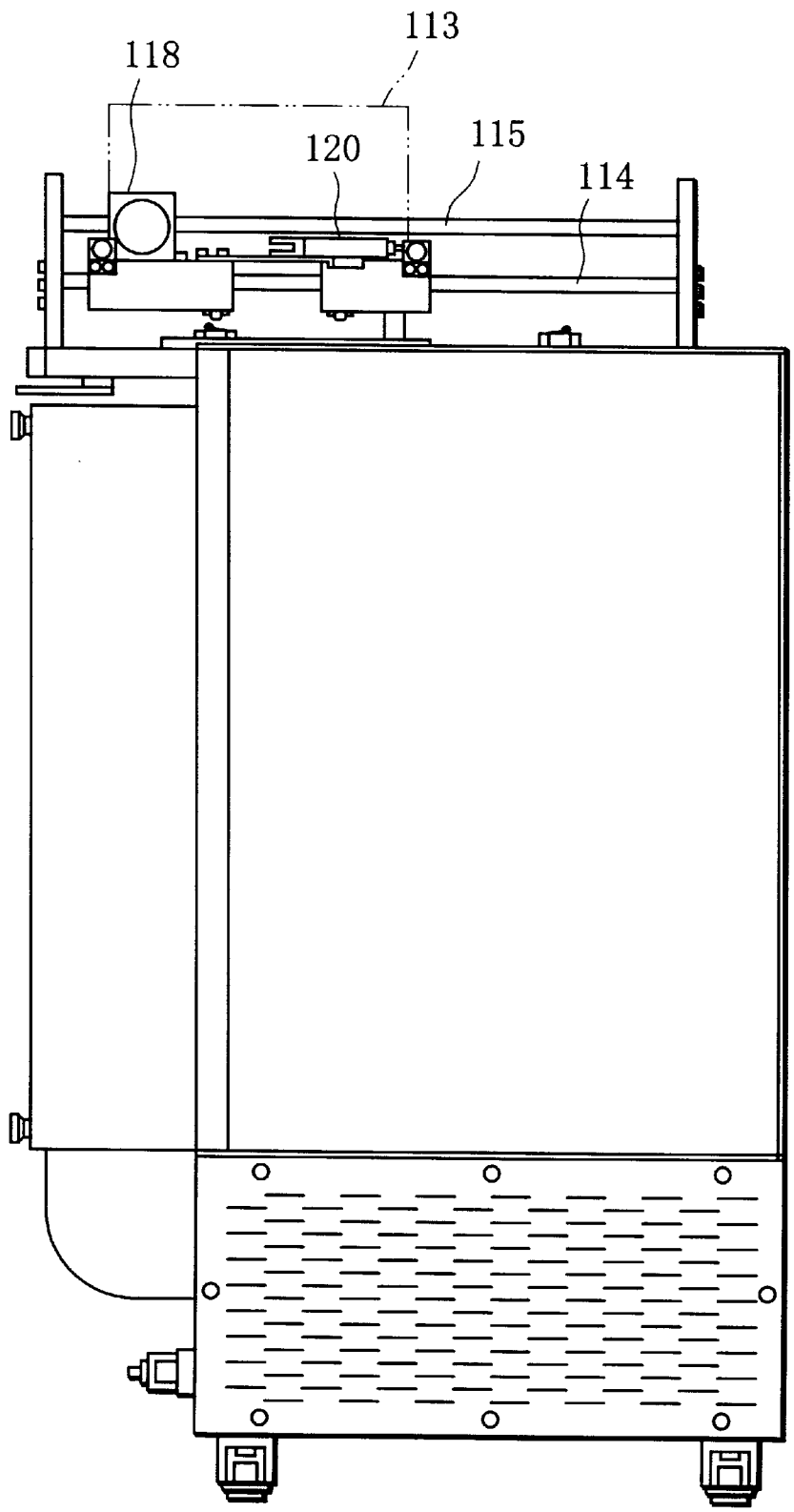
FIG. 22 is a front view showing the cigarette testing apparatus the primary part is shown in FIGS. 6 and 7.
Figure 23:
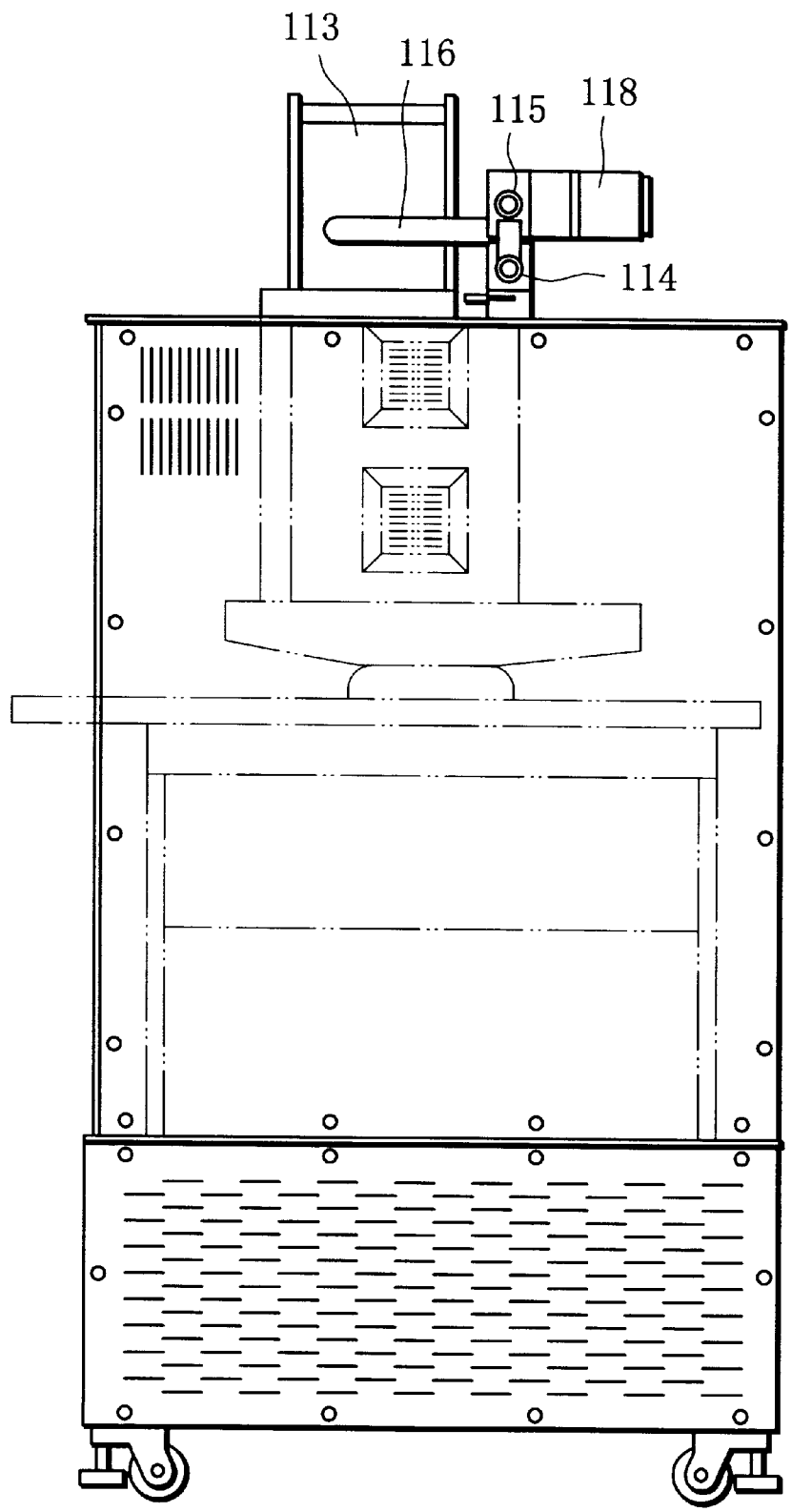
FIG. 23 is a side view of the cigarette testing apparatus shown in FIG. 22.

The cigarette testing apparatus, having an appearance shown in FIGS. 22 and 23, comprises a cigarette supplying section 100 for supplying cigarettes serving as test pieces, a weight measuring section 200 for measuring the weight of a cigarette, a circumference measuring section 300 for measuring the diameter or the circumference of a cigarette, a ventilation-characteristic measuring section 400, having a ventilation vessel, for measuring the ventilation resistance and ventilation characteristics of a cigarette, and a length/hardness measuring section 500 for measuring the length and the hardness of a cigarette. These apparatus sections 100, 200, 300, 400 and 500 operate under the control of a control section 700 (FIG. 9) equipped with a microprocessor and the like. The control section 700 is comprised of output ports through which various control signals are delivered, and input ports through which detection signals and pieces of detection data are received. In FIG. 6, reference numeral 800 denotes an ejection box for receiving cigarettes having been subjected to the measurements or testing.

Each of cigarettes stored in a supply box of the cigarette supplying section 100 is supplied from the cigarette supplying section 100 to the weight measuring section 200 where the weight of the cigarette is measured. Next, the cigarette is transferred onto revolving rollers of the circumference measuring section 300 and the diameter of the cigarette is measured while the cigarette is rotated on the rollers. After axially delivered from the rollers, the cigarette is held in a rotary holder, is changed in posture to a vertical position as the rotary holder rotates, and is caused to fall into the ventilation vessel of the ventilation-characteristic measuring section 400 in which ventilation characteristics of the cigarette are measured. Subsequently, the cigarette is delivered from the ventilation vessel into a rotary holder disposed below the vessel, is changed in posture to a horizontal position with rotation of this rotary holder, and is transferred onto a measuring stage of the length/hardness measuring section 500 where the length and the hardness of the cigarette are measured in sequence. Finally, the cigarette is ejected from the measuring stage and falls into the ejection box 800.

Cigarette supplying apparatus

Figure 7:
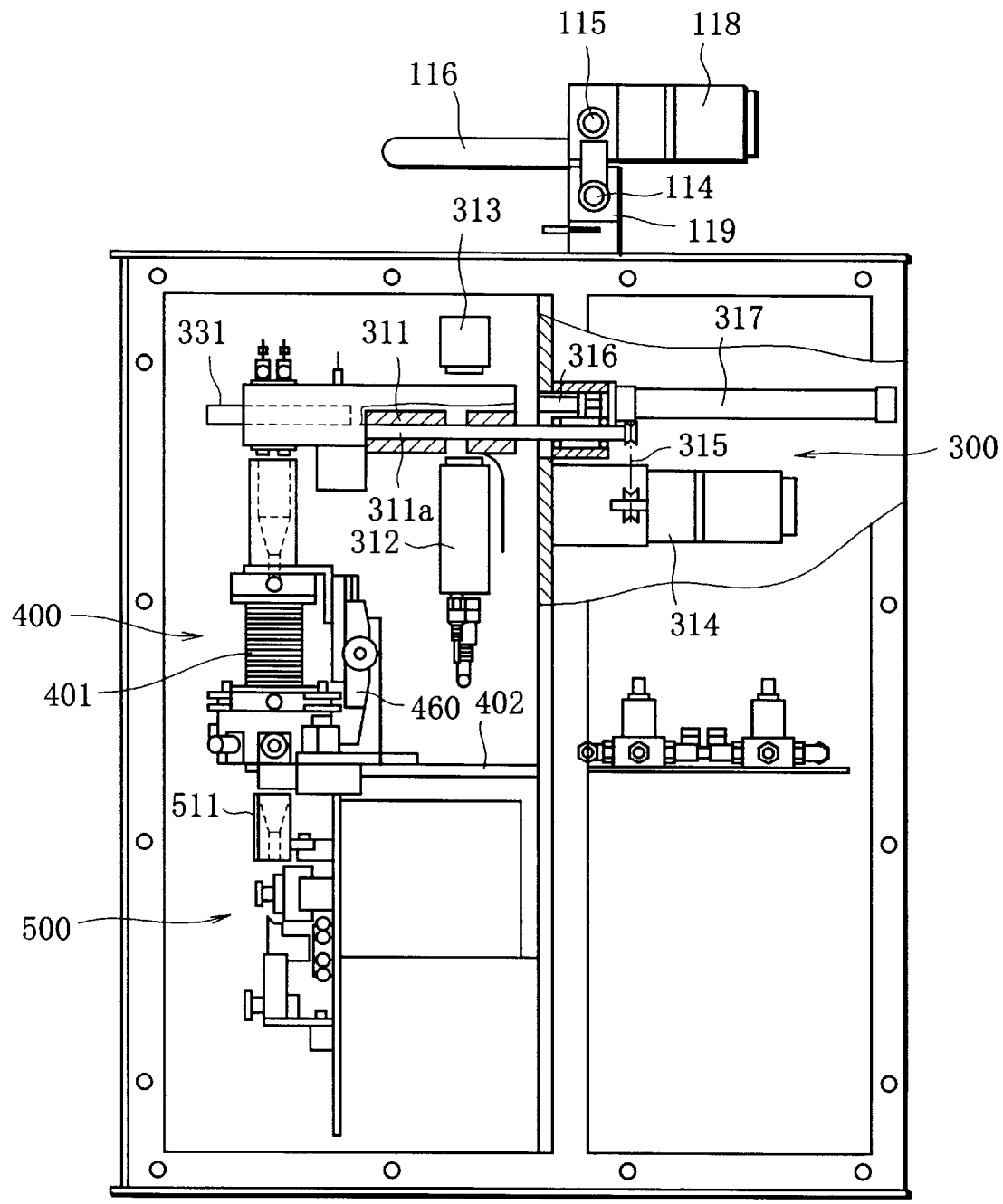
FIG. 7 is a side view of a primary part of the cigarette testing apparatus shown in FIG. 6.
Figure 8:
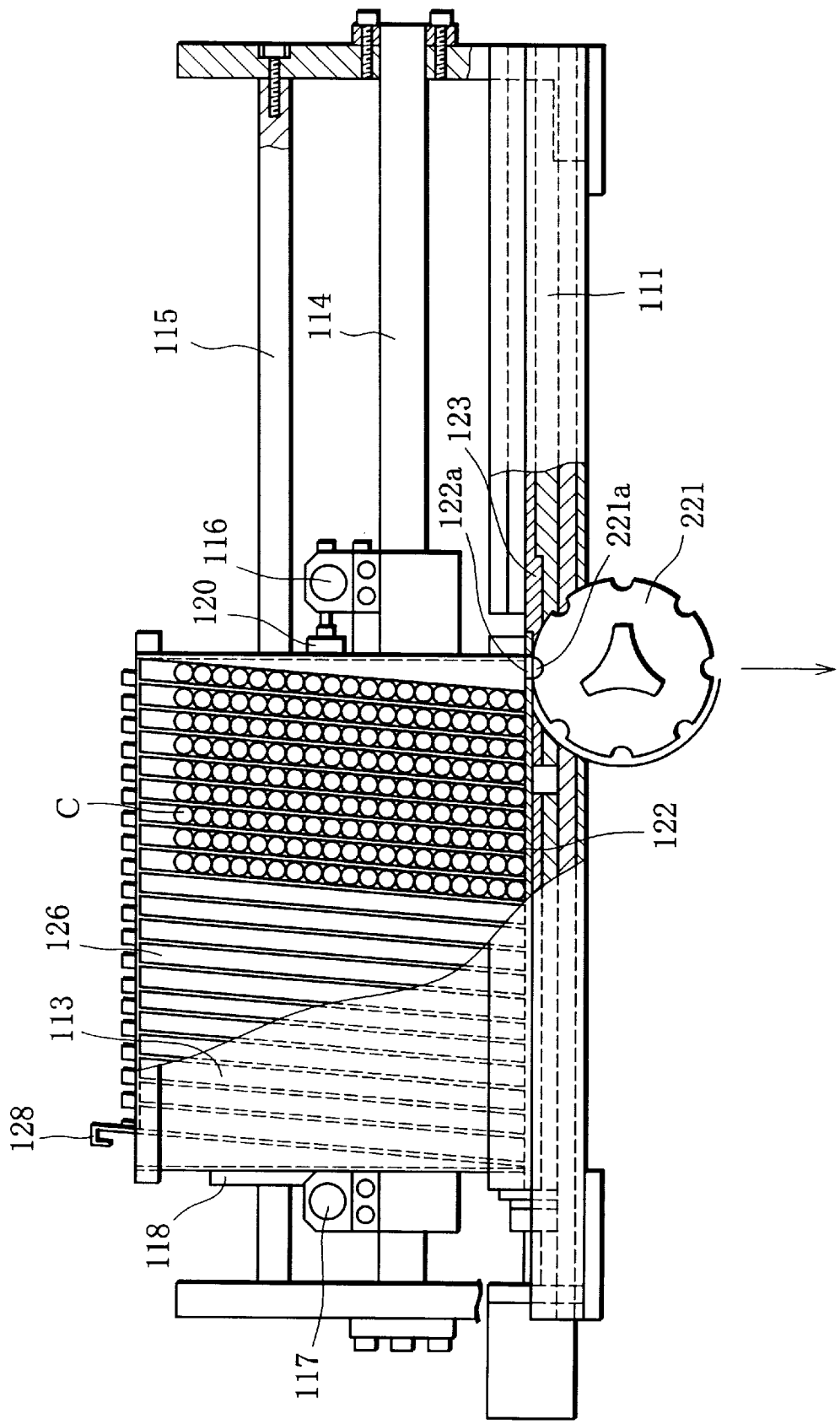
FIG. 8 is an enlarged front view of the cigarette testing apparatus shown in FIG. 6.

Referring to FIGS. 6, 7 and 8, a supply box 113 is supported by positioning guides (not shown) so as to be movable to the left side and to the right side in FIGS. 6 and 8, the positioning guides being fixed on the both sides of a supply stage 111. A ball-splined shaft 114 and a rack 115 are mounted on the supply stage and extend in the direction along which the positioning guides extend. First and second arms 116, 117 are coupled to the ball-splined shaft 114. The first arm 116, which mainly serves to regulate the position of the supply box 113, is abutted against one end of the supply box 113 and operates in an interlocking manner with the drive of a motor 118 mounted on the rack 115, via a journal 119. In particular, the first arm has a function of causing the supply box 113 to move to the left side in FIG. 6 during the movement of the supply box 113 to its return position. The second arm 117 which is directly coupled to the motor 118 is engaged with another end of the supply box 113 for moving the supply box to the right side.

In FIGS. 6 and 8, reference numeral 120 denotes a cylinder for the first arm. The cylinder 120 is actuated when the supply box 113 reaches a predetermined position, to cause the first arm 116, directly coupled to the cylinder 120, to be brought in press-contact with the supply box 113, to thereby hold the supply box at this press-contact position.

A plate-like shutter 122 (FIG. 8) is supported by shutter guides, not shown, so as to be movable in the direction along which the supply box moves. The shutter guides are provided on the both sides of a lower portion of the supply box 113, and the shutter 122 is disposed to face a bottom portion of the supply box 113. The shutter 122 serves as bottom plates of trays 126 accommodated in the supply box 113 and prevents test pieces (cigarettes) from falling from the trays. The shutter 122 is formed into a plate shape, and has a distal end thereof formed with a supply port 122a through which only one test piece passes and a rear end thereof having a T-shaped engaging portion (not shown). Preferably, the supply port 122a has its width wider than the width of the opening portion of the tray by approximately 1 mm.

A shutter stopper 123 for regulating the position of the shutter 122 is mounted to the supply stage 111. In order to regulate the position of the shutter 122, the shutter 122 is pressed through a pusher (not shown) by a cylinder 132 for the shutter, so that a distal end of the shutter is brought in contact with a stepped portion of the shutter stopper 123.

As shown in FIG. 8, a plurality of trays 126 are arranged and received in the supply box 113. Although detailed illustrations are omitted in the drawings, each of the tray 126, made of a synthetic resin having a small specific heat (such as ABS resin, vinyl chloride resin, and acrylic resin), has a slanted bottom plate and side walls. A guide for a stacking operation is provided in each side wall of the tray, and ventilation slits are formed in the bottom plate of the tray.

The tray 126 has a test-piece receiving section which is defined by the side walls and the bottom plate of the tray. The test-piece receiving section has its width of 125 mm, corresponding to the distance between the side walls, which is greater than lengths of commercial cigarettes which vary from about 70 mm to 120 mm, the depth of about 9 mm which is slightly greater than diameters of commercial cigarettes, and the length of about 180 mm which permits a package of about twenty cigarettes can be arranged in the test-piece receiving section.

With this tray 126 having the slanted bottom plate, test pieces are easily positioned and orientated so as to be aligned in a line. Because the stacking guide is provided in each tray, about twenty trays can be easily stacked relative to another with a predetermined distance. Generally, the quality testing on cigarettes is carried out after these cigarettes are subjected to a humidity control for about one week in a room maintained at a temperature of 20° C. and a humidity of 60% RH in order that tobacco shreds of the cigarettes have a 12% WB moisture content. For the humidity control, the trays 126 formed with a number of ventilation slits can be used as humidity control boxes. Thus, the frequency of test-piece handling operations for the humidity control and resultant damages to the test pieces can be reduced.

A spacer 128 is inserted between the last tray disposed in the supply box 113 and the inner wall of the supply box, to thereby prevent the trays from being displaced. As a consequence, the accuracy in positioning the opening portion of each tray in alignment with the supply port 122a formed in the shutter is improved, whereby test pieces can be delivered in a stable manner.

Operations of the supplying apparatus will be explained hereinbelow.

Trays 126 each receiving a package of twenty test pieces are stacked together and are placed in a room which provides a prescribed environment for humidity control. Subsequently, the trays 126 are mounted to the supply box 113. To this end, the shutter 122 is inserted into the shutter guides, and the trays containing test pieces are stacked relative to another from below in the supply box 113. After the last tray is stacked, the spacer 128 is inserted to thereby fix the trays to the supply box 113. Next, the supply box is set up such that openings of the trays are directed downward.

Subsequently, the supply box 113 is set between the positioning guides. Next, the cylinder for the shutter is actuated to press the shutter 122 against the shutter stopper 123 though the shutter pusher, to thereby position the supply port 122a formed in the shutter.

After the setting of the supply box 113 is completed, the motor 118 is actuated. As a result, the supply box 113 is pressed by the second arm 117 directly coupled to the motor 118 with a rack, and is slid on the fixed shutter 122 to move toward the supply drum. When the opening of the first tray coincides with the supply port 122a of the shutter, a photosensor (not shown) detects this, and the motor 118 is caused to stop. At the same time, the cylinder 120 for the first arm is operated, so that the supply box 113 is pressed and held by the first arm 116. Test pieces are discharged one by one due to their own weights toward the supply drum through the supply port 122a.

When the discharged number of test pieces counted by a photoelectric sensor, not shown, reaches the number of the test pieces accommodated in each tray, the motor 118 is actuated again, so that the supply box 113 slides on the shutter 112 until the next tray reaches a position right above the supply port 122a. This moving distance of the supply box can be detected by a detector which is comprised of a photoelectric sensor fixed to a main body of the supplying apparatus and a pulsive reflector provided on a bottom face or a side face of the supply box, for instance. Alternatively, the drive of the motor 118 may be controlled such that the supply box 113 is moved by the distance between adjacent trays.

The above-mentioned operations of positioning each tray and of discharging test pieces are repeated. When the last test piece of the last tray is discharged, the motor 118 is actuated to cause the supply box 113 to slightly move to the right side in FIGS. 6 and 8, to thereby actuate a limit switch 131 for returning the supply box. In response to the actuation of the limit switch 131, the motor 118 rotates reversely, so that the supply box 113 is pressed by the first arm 116 to move to the left side in FIGS. 6 and 8. When the supply box 113 returns to its initial position to actuate a limit switch 132 for detection of initial position, the motor 118 comes to a stop to cause the supply box 113 to stop at the initial position. Whereupon, the cylinder for the shutter and the cylinder 120 for first arm are rendered inoperative, whereby the supply box 113 becomes detachable from the supply stage 111.

Weight measuring section

Figure 9:
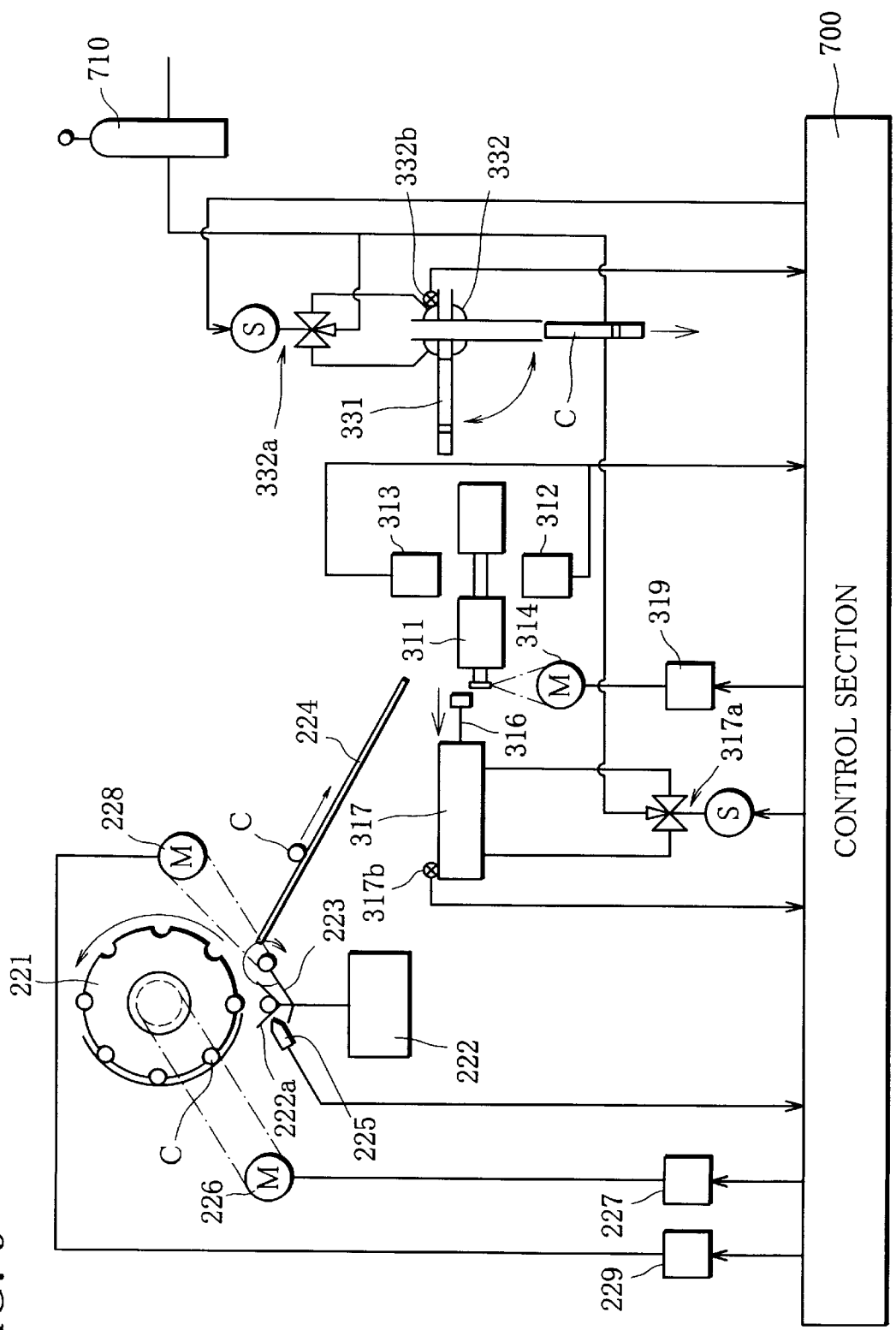
FIG. 9 is a schematic diagram showing a control system for a weight measuring section and a circumference measuring section of the cigarette testing apparatus shown in FIGS. 6 and 7.

As shown in FIGS. 6, 7 and 9, a weight measuring section 200 comprises a supply drum 221 having an outer peripheral face formed with a plurality of grooves 221a and an electric balance 222 having a weighing stage 222a, and is adapted to measure the weight of a test piece C supplied from a groove 221a formed in the supply drum 221 when the supply drum 221 is rotated through predetermined angles by a supply drum motor 226 (FIG. 9). The weight measuring section 200 further comprises an ejecting pawl 223 rotatable one turn by an ejecting pawl motor 228, and is adapted to lift the test piece, having been subjected to the weight measurement, from the weighing stage 222a by means of the ejecting pawl 223 to thereby eject the test piece toward a shoot 224. The ejected test piece rolls on the shoot 224 and is supplied to a circumference measuring section 300.

Circumference measuring section

Referring to FIGS. 6, 7 and 9, the circumference measuring section 300 comprises a pair of test-piece revolving rollers 311 which are disposed in a horizontal position. Each roller 311 is comprised of a rotary shaft 311a on which two short cylindrical blocks are mounted so as to be spaced from each other in the axial direction of the rollers. The rotary shafts of the revolving rollers 311 are coupled to a revolving roller motor 314 through timing belts 315. When driven by the motor 314, the revolving rollers 311 rotate in the same direction. During a diameter measurement on the test piece, the test piece placed on the revolving rollers 311 and extending in parallel to the longitudinal direction of the rollers 311 are rotated.

The circumference measuring section 300 further comprises a transmitter 312 and a receiver 313 which are disposed perpendicularly to the longitudinal axes of the revolving rollers 311 and which face each other. The transmitter 312 is adapted to project a laser beam having a width wider than the diameters of test pieces and a predetermined quantity of light. The receiver 313 is adapted to receive a laser beam projected from the transmitter 312 and output a voltage varying in dependence on a quantity of light which the receiver receives.

When no test piece is placed on the revolving rollers 311, the laser beam projected from the transmitter 312 to the receiver 313 through a gap between the revolving rollers 311 is not screened by a test piece, so that the receiver 313 generates a predetermined output voltage corresponding to a state where the laser beam is not screened. On the other hand, when a test piece is placed on the rollers 311, part of the laser beam is screened by the test piece, so that the output voltage of the receiver 313 decreases. An amount of decrease in the output voltage represents a screened width of the laser beam and hence represents the diameter of the test piece.

In case of using the transmitter 312 and the receiver 313 constituted by a laser type determination sensor (LX-130) manufactured by Keyence corporation, the measuring width of a laser beam is 10 mm, and the diameter D of a test piece is represented by the following equation which is in turn represented as a function of the output voltage E varying from 1 V at the time when the laser beam is fully screened to 5 V at the time when it is not screened.

$$D = K1 - K2 \times E$$

where coefficients K1 and K2 determined experimentally are equal to 12.3146 mm and 2.4171 mm/V, for instance.

The circumference measuring section 300 comprises a pusher 316 for ejecting a test piece from the revolving rollers 311, a pusher cylinder 317 for moving the pusher 316 back and forth, a rotary holder 331 provided with a cylinder portion having an inner diameter slightly larger than diameters of test pieces so as to permit a test piece ejected from the revolving rollers 311 to be inserted thereinto, a rotary holder cylinder 332 for reciprocally rotating the rotary holder 331 between a horizontal position and a vertical position. The rotary holder cylinder 332 has a cylinder shaft fitted to a cylindrical stationary portion which is formed integrally with the cylinder portion of the rotary holder 331 at an axially central part of the cylinder portion.

The pusher cylinder 317 is connected to a pressurized-air source 710 through a pipe in which a solenoid valve 317a for directional control is provided, and is turned ON and OFF depending on the switching position of the solenoid valve 317a. When the pusher cylinder 317 is turned ON, the pusher cylinder 317 causes the pusher 316 to move forward, so that a test piece placed on the revolving rollers 311 is inserted into the rotary holder 331 which is in a horizontal position. On the other hand, when the pusher cylinder 317 is turned OFF, the pusher 316 is moved backward to the pusher cylinder 317 side. With the backward movement of the pusher 316, a pusher detecting switch 317b attached to the pusher cylinder 317 is changed over from an OFF position to an ON position.

The rotary holder cylinder 332 is connected to the pressurized-air source 710 through a pipe in which a solenoid valve 332a for directional control is provided, and is turned ON and OFF in dependence on the switching position of the solenoid valve 332a. When the rotary holder cylinder 332 is turned OFF, the rotary holder cylinder 332 operates the rotary holder 331 to rotate from a horizontal position to a vertical position. When the rotary holder 331 is in a vertical position, the test piece in the rotary holder falls from the holder downward. On the other hand, when the rotary holder cylinder 332 is turned ON, the rotary holder cylinder 332 causes the rotary holder 331 to rotate from the vertical position to the horizontal position. The rotary holder detecting switch 332b is turned ON when the rotary holder 331 is in the horizontal position.

Control System for Circumference Measuring Section

When the presence of a test piece on the weighing stage 222a is detected by a detection sensor 225 in a condition that the pusher 316 is at the receding position and the holder 331 is in the horizontal position, so that both the pusher detecting switch 317b and the rotary holder detecting switch 332b are in ON positions, the ejecting pawl motor 228 is driven by a controller 229 under the control of the control section 700, whereby the ejecting pawl 223 is rotated to thereby cause the test piece to be transferred onto the revolving rollers 311.

Subsequently, when the test piece C is detected based on the output of the receiver 313, an ON control signal is delivered from the control section 700 to a controller 319, so that the revolving roller motor 314 is actuated to thereby cause the test piece C on the revolving rollers 311 to rotate.

Next, the output voltage of the receiver 313 is read, and the read data is stored in a memory. Further, an index indicative of the number of times the data is read is incremented. Until the number of data-reading times reaches a prescribed value, the output voltage of the receiver 313 is read at intervals of a predetermined sampling cycle, and pieces of read data are stored in the memory in sequence. After the output voltage data detected by the receiver 313 is stored a prescribed number of times in the memory, an OFF control signal is delivered to the controller 319, so that the motor 314 comes to a stop.

Next, the pusher cylinder 317 is turned ON for a predetermined period of time, so that the pusher 316 moves to cause the test piece on the revolving rollers 311 to be received in the rotary holder 331. When the pusher cylinder 317 is turned ON, the pusher 316 returns to the original position.

Subsequently, the rotary holder cylinder 332 is turned ON for a predetermined time period, so that the rotary holder 331 rotates from a horizontal position to a vertical position to cause the test piece to fall from the rotary holder downward. When the rotary holder cylinder 332 is turned OFF, the rotary holder 331 rotates from the vertical position to the horizontal position.

Pieces of data on the receiver output voltage are read out from the memory in sequence, and test-piece diameters for evaluation of complete circle of the test piece are calculated based on the pieces of data on the receiver output voltage. The diameter calculation is repeatedly carried out in respect of all of the pieces of output voltage data. For instance, the complete circle evaluation is made based on the maximum value and the minimum value among the calculated diameters. Furthermore, an average value of the calculated diameters is determined as the diameter of the test piece, and the circumference of the test piece is calculated from the thus determined test-piece diameter.

In this manner, the circumference of the test piece is accurately determined in a non-contact process without being affected by ventilation characteristics and hardness of the test piece or cigarette.

Ventilation Characteristic Measuring Section

Figure 10:
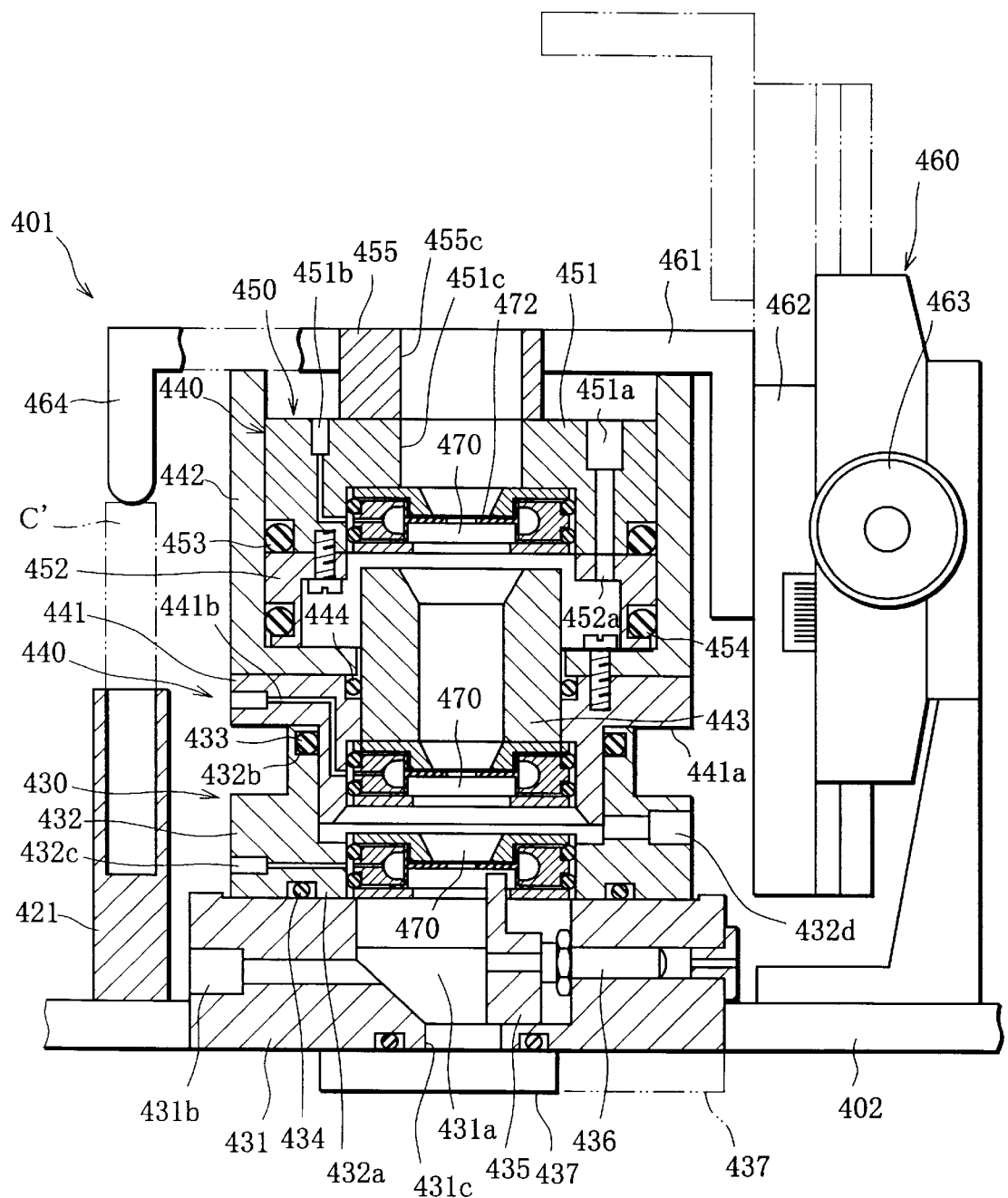
FIG. 10 is a sectional view schematically showing a construction of a ventilation vessel of the ventilation-characteristic measuring apparatus of the aforementioned preferred embodiment of the present invention.

Referring to FIGS. 6, 7 and 10, a ventilation-characteristic measuring apparatus which constitutes a ventilation-characteristic measuring section 400 of the cigarette testing apparatus comprises a ventilation vessel 401. The ventilation vessel 401 is comprised of first, second and third cylindrical containers 430, 440 and 450. The first cylindrical container 430 is fixed to a base plate 402. The third cylindrical container 450 is located coaxially with the first cylindrical container 430 above the first container and is mounted to a hoisting and lowering apparatus 460 which is in turn mounted to the base plate 402, so that the vertical position of the third cylindrical container 450 is adjustable by means of the hoisting and lowering apparatus 460. The second cylindrical container 440 is slidably air tightly fitted to an inner peripheral face of the first cylindrical container 430. The third cylindrical container 450 is slidably air tightly fitted to an inner peripheral portion of the second cylindrical container 440, whereby the second cylindrical container 440 is supported by the first and third cylindrical containers 430 and 450 coaxially therewith.

The first cylindrical container 430 is comprised of a first annular block 431 fixed to the base plate 402, and a second cylindrical block 432 fixed to an upper face of the first block 431 coaxially therewith. The second block 432 is provided at its lower portion with a flange 432a projecting radially inwardly thereof, so as to fittedly hold a test-piece supporting device 470 on the inner peripheral face of the flange 432a. Further, the second block 432 is configured such that the second cylindrical container 440 is slidably airtightly fitted to and held by the inner peripheral face of the second block 432 above the flange 432a. In order to ensure the airtightness between the second block 432 and the second cylindrical container 440, an O-ring 433 is fittedly disposed in an annular O-ring groove 432b formed in an inner wall face of the second block 432. In relation to an evacuation associated with a test-piece holding function of the test-piece supporting device 470, a communication hole 432c is formed in a peripheral wall of the flange 432a.

Figure 16:
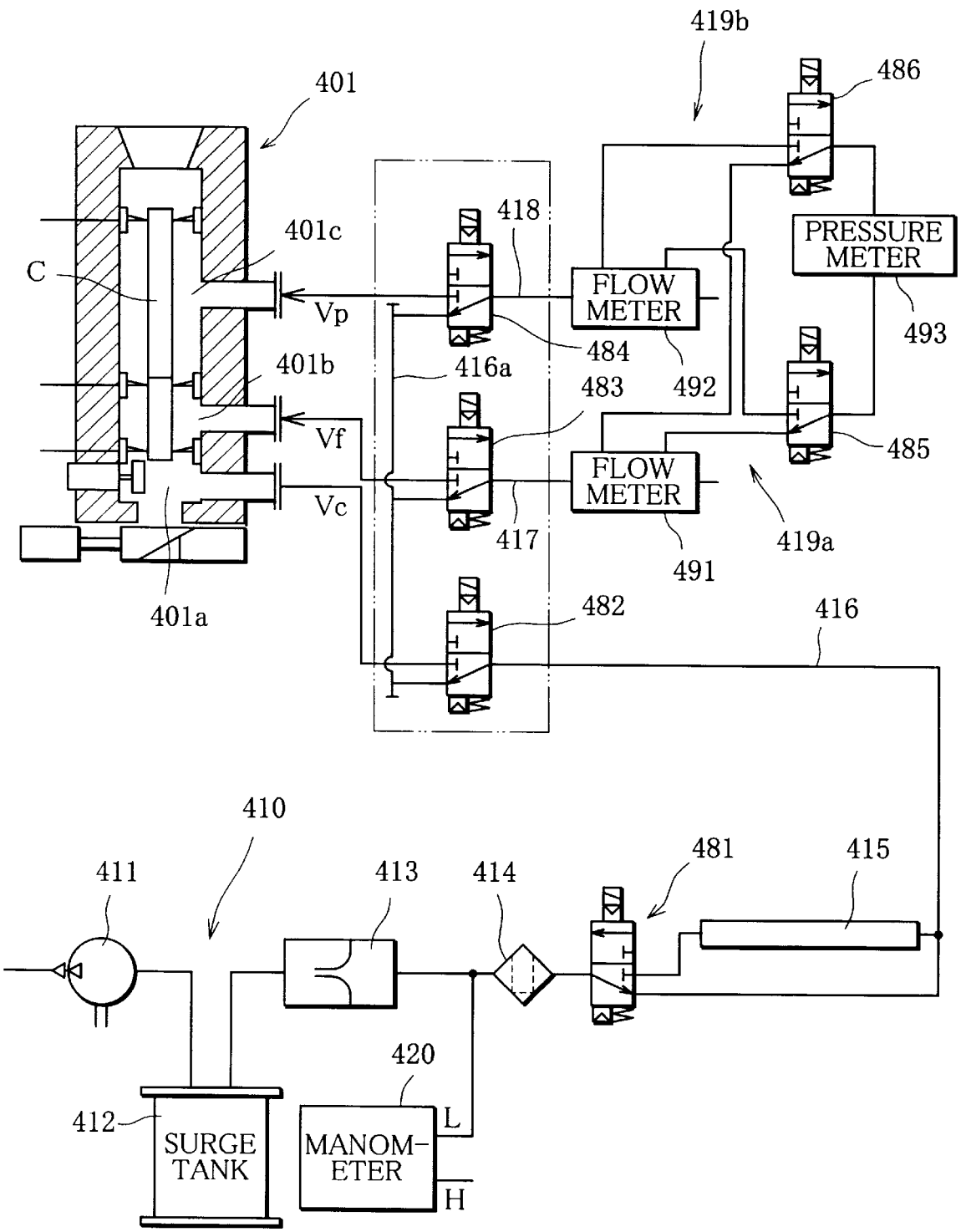
FIG. 16 is a schematic view showing an evacuating system and a flow rate detecting system of the ventilation-characteristic measuring apparatus shown in FIG. 10.

The first block 431, having an upper face to which the second block 432 is airtightly fixed through the O-ring 434, is formed at its central part with a cylindrical space 431a corresponding to a first airtight chamber (shown by reference numeral 401a in FIG. 16). An upper end opening of the first block 431 has its diameter slightly smaller than the outer diameter of the test-piece supporting apparatus 470 and is located at a location radially inwardly with respect of an inner peripheral face of the flange 432a, so as to regulate the =position at which the test-piece supporting device 470 is fittedly mounted to the inner peripheral face of the flange 432a.

A stopper 435 adapted to abut against an end face of a cigarette C, as a rod-shaped test piece, for regulating the position of the cigarette C is provided in the space 431a of the first block 431 so as to be movable back and forth in the lateral direction. The stopper 435 is ordinarily positioned at a receding position laterally away from a center part of the space 431a. At the time of positioning the cigarette, on the other hand, the stopper is positioned at the center part of the space, i.e., at a cigarette holding position, by the action of an air cylinder 436 accommodated in the first block 431. The first block 431 is formed at its side wall with a suction hole 431b through which the space 431a is evacuated at a predetermined flow rate, and a shutter mechanism 437 for selectively opening or closing a lower end opening of the first block is provided at a lower face of the first block 431.

The second cylindrical container 440 is comprised of a third cylindrical block 441 having a flange 441a formed at an upper end portion of the third block and projecting radially outwardly thereof, the test-piece supporting device 470 being fittedly mounted from below to a lower end portion of the flange 441a, a fourth cylindrical block 442 which is large in diameter and which is fixed to an upper face of the flange 441a of the third block 441 coaxially therewith, and a fifth cylindrical block 443 fittedly mounted to an inner peripheral face of the third block 441. The fifth block 443 serves as a guide member for guiding a cigarette C. The flange 441a of the third block 441 is configured such that its lower face is abutted against an upper face of the second block 432 of the first cylindrical container 430, to thereby regulate the maximum depth for which the third block 441 can be fitted into the second block 432. In other words, the minimum vertical mounting position of the second cylindrical container 440 relative to the first cylindrical container 430 is regulated.

Figure 11:
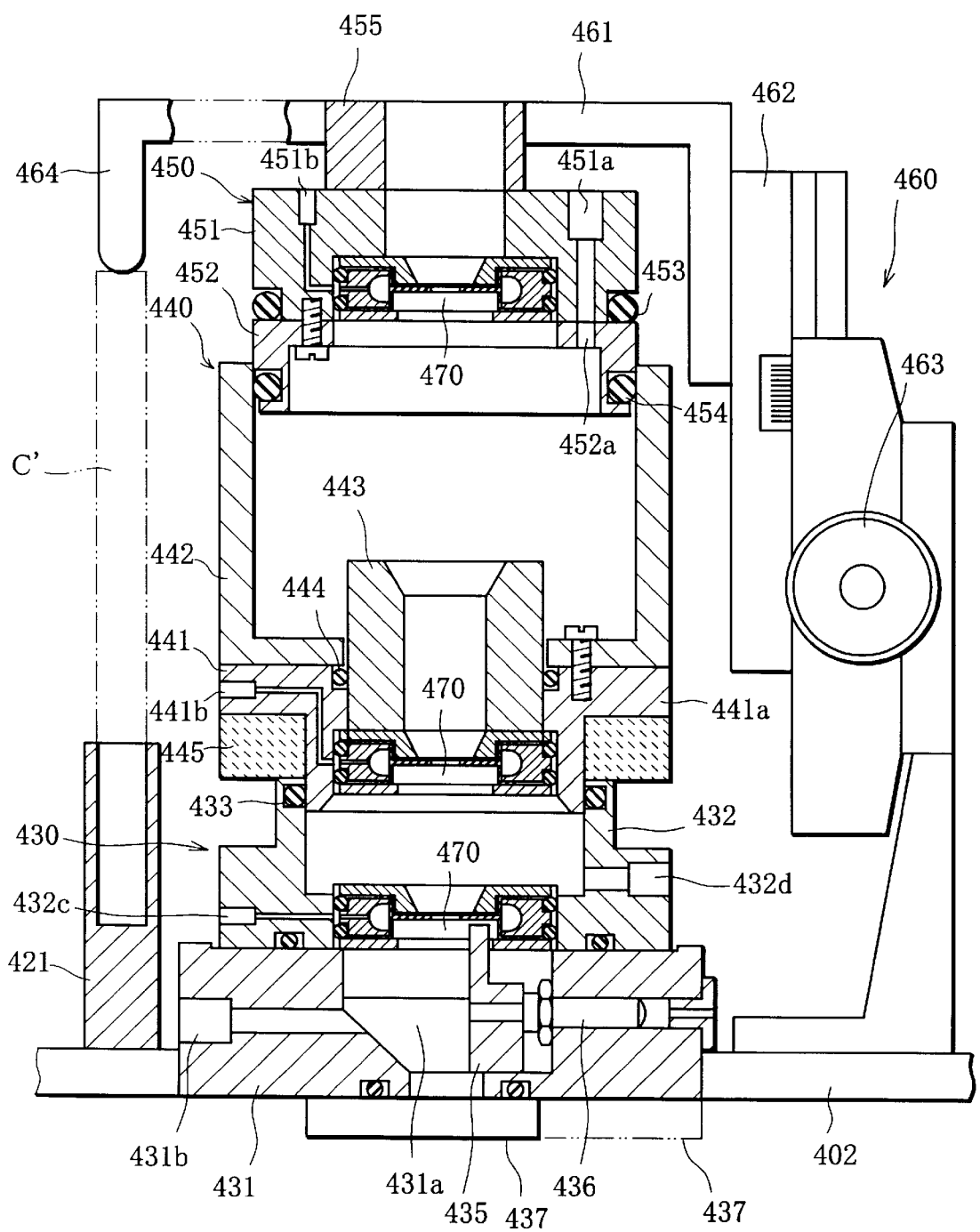
FIG. 11 is a view showing the ventilation vessel shown in FIG. 10 in a condition that a third cylindrical container is mounted to first and second cylindrical containers.

As shown by way of example in FIG. 11, an annular spacer 445 having a predetermined thickness may be interposed between the upper face of the second block 432 of the first cylindrical container 430 and the lower face of the flange 441a of the third block 441, so as to increase, by the spacer thickness, the vertical mounting position of the second container 440 with respect to the first cylindrical container 430 for an adjustment of the vertical mounting position.

An inner peripheral face of the third block 441 is formed with a stepped portion and has an upper end portion at which the fifth block 443 is held. The diameter of the upper end portion of the inner peripheral face is slightly smaller than the diameter of that lower end side of the inner peripheral face to which the test-piece supporting device 470 is mounted. With this arrangement, the mounting position of the test-piece supporting device 470 is regulated. The third block 441 is formed with a communication hole 441b in relation to an evacuation for acting the test-piece holding member of the test-piece supporting device 470. An O-ring 444 provides an airtight seal between the third block 441 and the fourth block 442. A second air tight chamber(shown by reference numeral 401b in FIG. 16) is defined by the third block 441, the second block 431, to which the third block 441 is fitted, of the first cylindrical container 430, and the test-piece holding members mounted to the second and third blocks. As the first airtight chamber is evacuated, air is introduced from the outside of the ventilation vessel 401 into the second airtight chamber through an air hole 432d formed in the second block 432.

The third cylindrical container 450 is comprised of a sixth cylindrical block 451 slidably airtightly fitted to the inner peripheral face of the fourth block 442, and a seventh cylindrical block 452 mounted to a lower end face of the sixth block 451 coaxially therewith. The sixth block 451 is formed with an opening 451c extending therethrough and permitting a test piece C to pass therethrough. The sixth block 451 is configured such that a test-piece supporting apparatus 470 is mounted to a lower portion of an inner peripheral face of the sixth block formed with a stepped portion, to thereby regulate the mounting position of the test-piece supporting device 470.

The sixth block 451 and the seventh block 452 are joined and fixed to each other through an O-ring 453, and an O-ring 454 is attached to an outer wall face of the sixth block 451 so as to be slidable relative to the cylindrical container 440. The sixth block 451 of the third cylindrical container 450 defines a third airtight chamber (shown by reference numeral 401c in FIG. 16) in cooperation with the second cylindrical container 440 and the test-piece holding members mounted to the second and third containers. Furthermore, the sixth block 451 is formed with a communication hole 451a in relation to an evacuation for acting on the test-piece holding member of the test-piece supporting device 470 attached to the sixth block 451. To be noted, the communication hole 451a has its outer opening end which is open to an upper face of the sixth block 451, so as to permit the introduction of air from the outside to the third airtight chamber even if the third cylindrical container is fitted in the second cylindrical container 440.

The seventh block 452 of the third cylindrical container has a lower end face thereof adapted to be abutted against an upper face of a bottom wall of the fourth block 442, to make it possible to regulate the maximum depth for which the third cylindrical container is permitted to be fitted into the fourth block 442 of the second cylindrical. When the seventh block is fitted into a peripheral wall of the fourth block 442 with a minimum depth, it serves to regulate the minimum fitting depth for which the third cylindrical container is fitted to the second cylindrical container. The third container 450 defines a third airtight chamber (shown by reference numeral 401c in FIG. 16) in cooperation with the second cylindrical container 440 and the test-piece holding members attached to the second and third containers. As the first airtight chamber is evacuated, air is introduced into the third airtight chamber through air holes 451a and 452a which are formed in the sixth block 451 and the seventh block 452 so as to be vertically aligned with each other.

An upper end portion of the sixth block 451 constituting part of the third cylindrical container 450 is fixed through a cylindrical supporting member 455 to an arm 461 which extends laterally of the third cylindrical container 450. The supporting member 455 is formed with an axial hole 455c for permitting a test piece C to pass therethrough in alignment with an axial hole 451c of the sixth block 451. The arm 461 is coupled to a vertically movable member 462 of a hoisting and lowering apparatus 460 mounted to the base plate 402. The vertical position of the arm 461 is adjusted through a rack and pinion mechanism, not shown, by rotating a dial 463 of the hoisting and lowering apparatus 460. By this height adjustment of the arm 461, the vertical position of the third cylindrical container 450 with respect to the base plate 402 as well as the vertical position of the third cylindrical container with respect to the first cylindrical container 430 are adjusted.

The base plate 402 is provided with a blind cylindrical holder 421, disposed laterally away from the first cylindrical container 430, for holding a positioning rod-shaped member such as a cigarette C' in parallel to the longitudinal axis of the ventilation vessel 401 comprised of the first, second and third cylindrical containers 430, 440 and 450. Preferably, the positioning rod-shaped member has the same shape and dimension as those of a test piece disposed in the ventilation vessel 401 and subject to a ventilation testing. The positioning cigarette C' is disposed at the same vertical position as that of the cigarette C positionally regulated by the stopper 435 and held in the ventilation vessel 401. By causing a distal end of the guide member 464 attached to the vertically movable member 462 of the hoisting and lowering apparatus 460 to be abutted against a distal end face of the positioning cigarette C' held in the holder 421, the vertical positions of the movable member 462 and the third cylindrical container 450 are adjusted while the cigarette C' is utilized as a positioning index.

The fitting depths between corresponding ones of the first, second and third cylindrical containers 430, 440 and 450 constituting the ventilation vessel are adjusted in accordance with a test piece (a filter cigarette C) received in the ventilation vessel and subject to testing. More specifically, the mounting height position of the second cylindrical container 440 is adjusted by interposing a spacer 445 having an appropriate thickness between the first container 430 and the second container 440. The vertical position of the third cylindrical container 450 relative to the first cylindrical container 430 is adjusted by the hoisting and lowering apparatus 460 while the cigarette C' held by the holder 421 is used as a positioning index.

The spacer may be obtained by cutting an annular member made of a hard rubber, for instance, into a C-shaped member which is elastically deformable. The spacer 445 kept in an expanded C-shaped form is attached to the outer peripheral face of the third block 441 of the second cylindrical container 440.

According to the ventilation vessel 401 comprised of the first, second and third cylindrical containers 430, 440 and 450 constructed as mentioned above, the third cylindrical container 450 is supported by the hoisting and lowering apparatus 460 such that the vertical position of the third container with respect to the first cylindrical container 430 fixed on the base plate 402 is adjustable, and the second cylindrical container 440 is fitted to the first and third cylindrical containers 430 and 450. In this manner, the mounting arrangement for the second container is extremely simplified. Particularly, in a condition that the third cylindrical container 450 is raised up to its uppermost vertical position, the second cylindrical container 440 can be easily mounted to and dismounted from the first cylindrical container 430 or the third cylindrical container 450 by utilizing a space between the first container 430 and the third container 450. Further, the third cylindrical container 450 is lowered by the hoisting and lowering apparatus 460 after the second cylindrical container 440 is mounted to one of the first and third containers 430, 450, whereby the second container 440 can be easily fitted to the other of the first and third containers. In this manner, the ventilation vessel can be easily assembled. The ventilation vessel can be easily disassembled into the first, second and third containers 430, 440 and 450 by reversing the assembly procedures.

Figure 5:
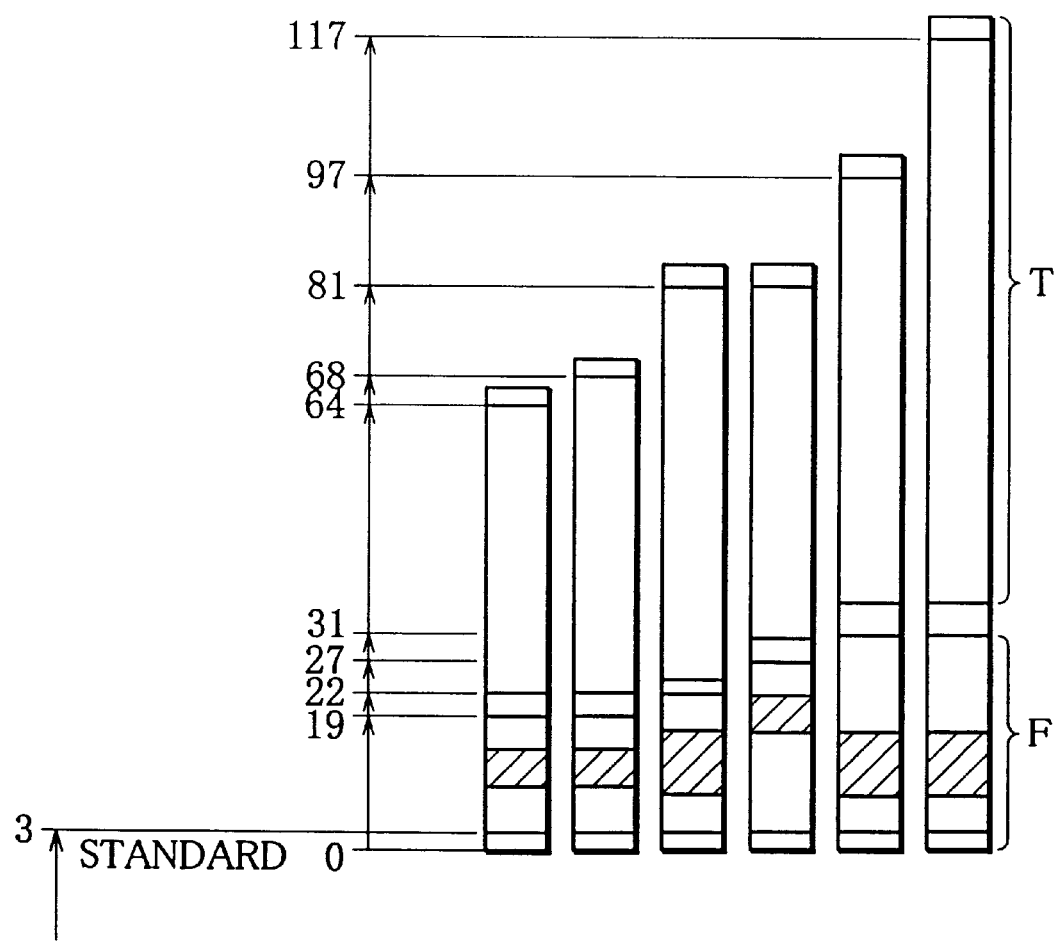
FIG. 5 is a view showing by way of example various types of cigarettes C mounted to a ventilation-characteristic measuring apparatus and subjected to testing.

With the above described arrangement, moreover, the distance (spacial interval) between the test-piece supporting devices 470 attached to the first and second cylindrical containers 430 and 440 can be easily varied and at the same time the airtightness between the first and second containers can be maintained by sliding the second container 440 relative to the first container 430. Similarly, the distance (spacial interval) between the test-piece supporting devices 470 attached to the second and third cylindrical containers 440 and 450 is easily variable while keeping the airtightness between the second and third containers by sliding the third container 450 relative to the second container 440. The vertical position of the third container 450 supported by the hosting and lowering apparatus 460 can be adjusted by using the cigarette C' held by the holder 421 as a positioning index, and the vertical position of the second container 440 relative to the first container 430 can be adjusted by using the spacer 445. Thus, by adjusting the thickness of the spacer 445 or using the spacer 445 having an appropriate thickness to thereby adjust the mounting vertical position of the second cylindrical container 440 and by adjusting the vertical position of the third cylindrical container 450 so as to meet the entire length of a cigarette C, the first, second and third containers 430, 440 and 450 can be positioned in such a manner that the cigarette C can be positioned in place irrespective of specifications thereof which vary as shown in FIG. 5. This makes it possible for the test-piece supporting devices 470, attached in place to the cylindrical containers 430, 440 and 450, to hold the cigarette C from the outer peripheral side of the cigarette such that a filter section F and a shredded tobacco section T of the cigarette C are separately positioned in the second and third airtightness chambers, respectively.

Under this condition, the space (first airtight chamber) 431a formed in the first block is evacuated at a predetermined flow rate Vc through the suction hole 431b. In this state, a flow rate Vf of air flowing through the air hole 432d into the second airtight chamber and then flowing into the first airtight chamber through the filter section F of the cigarette C is measured, and a flow rate Vp of air flowing through the air holes 451a, 452a into the third airtight chamber and then flowing into the first airtight chamber through the shredded tobacco section T of the cigarette C is measured. Subsequently, air inflow ratios for the filter and shredded tobacco sections of the cigarette C are determined for an evaluation of cigarette qualities.

Figure 12:
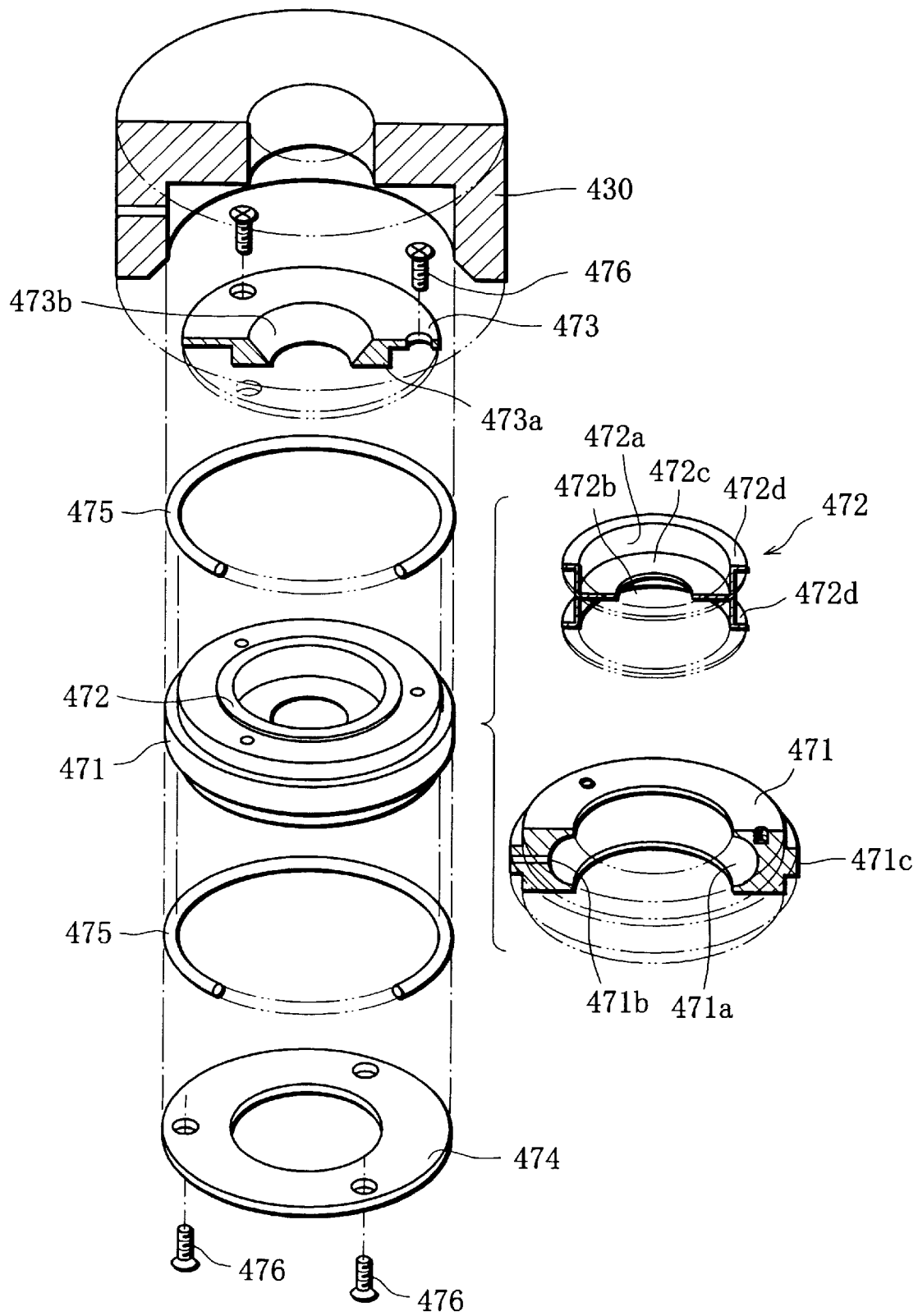
FIG. 12 is an exploded perspective view of a test-piece supporting device mounted to the ventilation vessel shown in FIG. 10.

Detailed explanations will be given with regard to the test-piece supporting device 470 mounted to each of the first, second and third cylindrical containers 430, 440 and 450. The test-piece supporting device 470 has its construction illustrated by way of example in FIG. 12.

The test-piece supporting device 470 is comprised of a ring-shaped holder 471 attached to the inside of each of the first, second and third containers 430, 440 and 450, and a test-piece holding member 472 mounted to an inner peripheral face of the holder 471 and made of a thin-walled elastic material such as rubber, an upper presser 473 for fixing the test-piece holding member 472 to the holder 471, a lower presser 474, and a pair of ring-shaped seal members (O-rings) 475 mounted to an outer peripheral face of the holder 471, for providing an airtight seal between the holder 471 and each of the cylindrical containers 430, 440 and 450 and for holding the holder 471 by an elastic force in the cylindrical container 430, 440 or 450.

The holder 471 is formed at a central part of the inner peripheral face thereof with a recess 471 which is semicircular in longitudinal section and which extends along the entire circumference of the inner peripheral face of the holder, and is formed with a communication hole 471b through which the recess 471a communicates with a central part of the outer peripheral face of the holder 471. Moreover, the holder 471 is formed at a central part of the outer peripheral face thereof with an annular projection (position-regulating portion) 471c for regulating positions at which the O-rings 475 are mounted, to thereby ensure the provision of an airtight space between the central part of the outer peripheral face of the holder and the cylindrical container 430, 440 or 450. The height (amount of projection from the outer peripheral face) of the annular projection 471c is set to approximately half the diameter of the O-rings 475. The communication hole 471b is open to a peripheral face of the annular projection 471c so as not to be closed by the O-rings 475.

The test-piece holding member 472 has a thin-walled tubular portion 472a having its height corresponding to the thickness of the holder 471 and its outer diameter corresponding to the inner diameter of the holder 471, and an annular flange 472c formed in and projecting from a central part of an inner wall face of the tubular portion 472a and having an inner peripheral edge thereof defining a test-piece supporting hole 472b. A pair of jaw portions 472d are provided at upper and lower ends of the tubular portion 472a. The test-piece holding member 472 comprised of the tubular portion 472a, flange 472c and jaw portions 472d may be made of a synthetic rubber material and may be formed into one-piece.

The test-piece holding member 472 having the above construction is flexed and fitted into a central hole of the annular holder 471, and is mounted thereto in such a manner that inner peripheral edge portions of the upper and lower faces of the holder 471 are sandwiched between the jaw portions 472d. An airtight space is defined by the tubular portion 472a of the test-piece holding member 472 mounted to the holder 471 and the recess 471a of the holder 471. This airtight space communicates with an airtight space, defined between the central part of the outer peripheral face of the holder 471 and the associated cylindrical container, through the communication hole 471b.

The test-piece holding member 472 attached to the holder 471 is fixed to the holder 471 so as not to be detached therefrom by means of the upper and lower pressers 473, 474 constituted by annular circular plates and attached to the upper and lower faces of the holder 471 through the jaw portions 472d of the test-piece holding member 472. The upper and lower pressers 473, 474 are mounted to the holder 471 by using screws 476, for instance. To be noted, the upper presser 473 is provided at its inner peripheral edge portion with a tubular portion 473a which intrudes into the center hole of the annular holder 471 to a predetermined depth. The tubular portion 473a has its inner peripheral edge portion formed into a truncated conical face whose diameter becomes smaller on the lower side thereof, to constitute a guide portion for introducing a rod-shaped test piece (cigarette C) supplied from above into the test-piece supporting hole 472b constituted by the inner peripheral edge of the flange 472c of the test-piece holding member 472.

Figure 13:
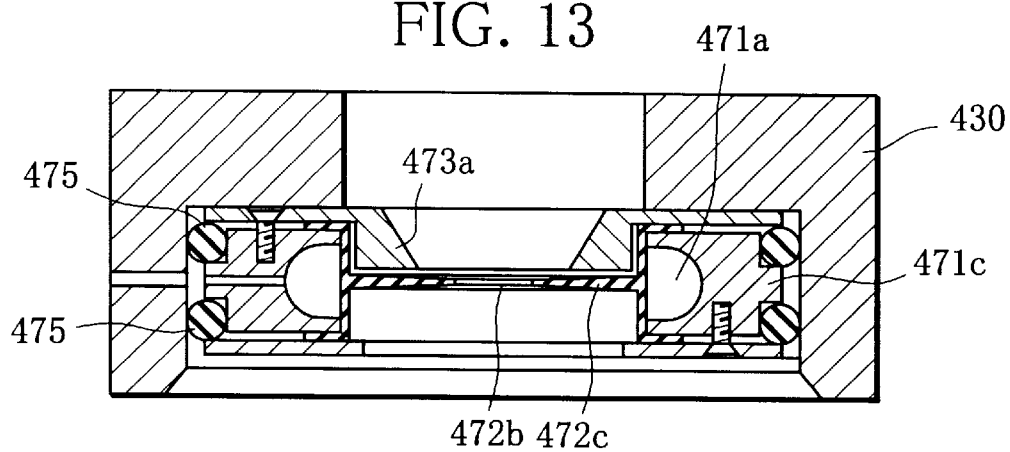
FIG. 13 is a view showing the test-piece supporting device shown in FIG. 12 in a state that it is mounted to the cylindrical container.

A pair of ring-shaped seal members (O-rings) 475 are fitted onto the outer peripheral face of the holder 471 from the upper and lower end sides of the holder, to which the test-piece holding member 472 is attached, at positions regulated by the annular projection (position-regulating portion) 471c which is formed in and projecting from the central part of the outer peripheral face of the holder 471, whereby the seal members 475 are prevented from being in contact with each other. The test-piece supporting device 470, in which the O-rings 475 are mounted to the outer peripheral face of the holder 471 as mentioned above, is disposed at a predetermined position inside the associated one of the cylindrical containers 430, 440 and 450, by exerting an elastic force of the O-rings 475 which are flexed as the test-piece supporting device is mounted to the cylindrical container as shown in FIG. 13. Each O-ring 475 is disposed between the inner peripheral face of the associated one cylindrical container 430, 440 or 450 and the outer peripheral face of the holder 471 to provide a seal, whereby an airtight space is formed between the inner peripheral face of the cylindrical container and that center part of the outer peripheral face of the holder 471 which is surrounded by the associated two O-rings 475.

Figure 14:
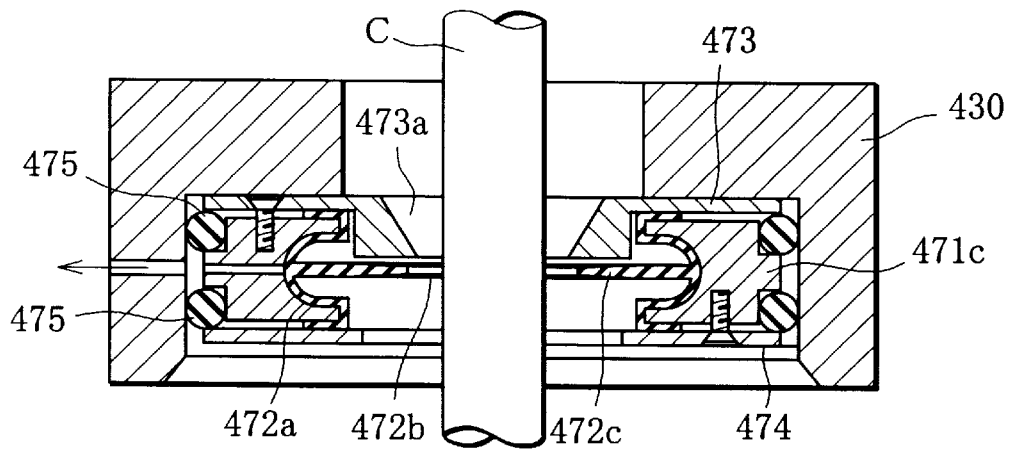
FIG. 14 is a view showing the test-piece supporting device shown in FIG. 12 in a state that a test piece is inserted thereinto.

As explained in the above, the communication holes 432c, 441b and 451b are formed in the peripheral walls of the cylindrical containers 430, 440 and 450 which cooperate with the outer peripheral face of the holders 471 to form the airtight spaces. When a respective recess 471a serving as an airtight chamber is evacuated through the communication hole 432c, 441b or 451b and the communication hole 471b formed in the holder 471, the tubular portion 472a of the test-piece holding member 47 is elastically deformed as shown in FIG. 14, to be sucked onto a wall face defining the recess 471a. With the deformation of the tubular portion 472a, the flange 472c is pulled outward, so that the diameter of the test-piece supporting hole 472b defined by the inner peripheral edge of the flange 472c increases.

Figure 15:
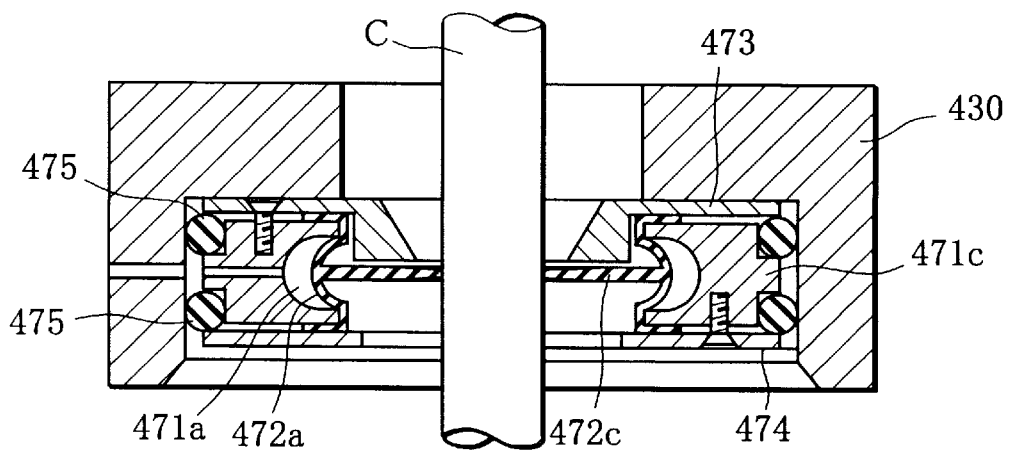
FIG. 15 is a view showing the test-piece supporting device shown in FIG. 12 in a state that a test piece is supported by the device.

In the condition that the test-piece supporting hole 472b increases in diameter, a rod-shaped test piece (cigarette C) is introduced into the test-piece supporting hole 472b as shown in FIG. 14. Subsequently, the evacuation of the recess 471a is terminated, so that the test-piece holding member 472 is elastically restored as shown in FIG. 15 and hence the diameter of the test-piece supporting hole 472b defined by the inner peripheral edge of the flange 472c decreases. Thus, the inner peripheral edge of the flange 472c abuts against the outer peripheral face of the test piece (cigarette C), and the test piece is held by an elastic restoration force produced by the flange.

According to the test-piece supporting device 470 constructed as explained above, the test-piece supporting device can be mounted to a corresponding one of the cylindrical containers 430, 440 and 450 simply by inserting the same while causing the O-rings 475, attached to the outer peripheral face of the holder 471, to be deformed. Thus, the operation of mounting the test-piece supporting device is very easy. Similarly, the test-piece supporting device can be very easily detached from the cylindrical container 430, 440 or 450 simply by pulling out the same against frictional forces produced by the O-rings 475.

The test-piece holding member 472 can be mounted to the holder 471 simply by causing the upper and lower faces of the holder 471 to be sandwiched between the jaw portions 472a of the test-piece holding member 472, so that no particular positional adjustment for the test-piece holding member is required in mounting the same to the holder, and the mounting of the test-piece holding member 472 can be made stably and reliably. Since the thus mounted test-piece holding member 472 is securely fixed with use of the upper and lower pressers 473, 474, an inadvertent detachment of the test-piece holding member 472 is advantageously prevented. Moreover, since the upper presser 473 includes the tubular portion 473b serving as a guide member, the test-piece supporting device can smoothly introduce a test piece (cigarette C) into the test-piece supporting hole 472b, without the need of employing a separately fabricated guide member.

As described in the above, the ventilation vessel 401 of the ventilation-characteristic measuring section 400 is arranged to define a first airtight chamber 401a around the lower end of a cigarette C held in the vessel, a second airtight chamber 401b around the filter section F of the cigarette C, and a third airtight chamber 401c around the shredded tobacco section T of the cigarette. Then, a flow rate Vf of air flowing from the outside of the ventilation vessel 401 into the second airtight chamber 401b and then flowing into the first airtight chamber 401a through the filter section F of the cigarette C and a flow rate Vp of air entering from the outside of the ventilation vessel into the third airtight chamber 401c and then flowing into the tobacco section T of the cigarette C are measured in the ventilation-characteristic measuring section 400 in the form of pressure, as the first airtight chamber 401a is evacuated.

To this end, the ventilation-characteristic measuring section 400 comprises an evacuation system and a flow rate measurement system shown in FIG. 16 where the illustration of the ventilation vessel 401 is simplified.

Referring to FIG. 16, the ventilation-characteristic measuring section 400 comprises a suction system 410 which in turn comprises a surge tank 412 evacuated by a vacuum pump 411, a critical nozzle 413 sucked through the surge tank 412, and a mist filter 414 disposed on the upstream side of the critical nozzle 413 as viewed from the pump 411 side. The critical nozzle 413 serves to generate a stream of air at a constant flow rate of 17.5 ml/sec, for instance, by causing a fixed volume of air to flow in its nozzle section at a sound velocity under a predetermined pressure. The suction system 410 is permitted to be connected through a pipe 416 to the first airtight chamber 401a of the ventilation vessel 401. A first and second three-way valves (SV1, SV2) 481, 482 are provided in the pipe 416. When the first three-way valve 481 is turned ON, a standard test piece 415 is inserted in the pipe 416. When the second three-way valve 482 is turned ON, the suction system 410 is connected to the first airtight chamber 401a of the ventilation vessel 401.

A third three-way valve (SV3) 483 is provided in a pipe 417 through which the second airtight chamber 401b of the ventilation vessel 401 is connected to a first resistance-type flow meter 491, and a fourth three-way valve (SV4) 484 is provided in a pipe 418 for connecting the third airtight chamber 401c with a second resistance-type flow meter 492. Each of the resistance-type flow meters 491 and 492 produces a pressure difference between an inlet port side and an outlet port side thereof in accordance with a flow rate of air passing therethrough. Pressure difference pipes 419a, 419b of the flow meters 491 and 492 are permitted to be connected to a pressure meter (minute pressure-difference sensor) 493 through fifth and sixth three-way valves (SV5, SV6) 485 and 486, so that a pressure difference (air flow rate) produced in each flow meter 491 or 492 is measured by the pressure meter 493. The valves 485 and 486 serve as pressure-system changeover valves which make switching actions in an interlocking manner.

When the second three-way valve 482 is turned OFF so that the suction system 410 is disconnected from the first airtight chamber 401a of the ventilation vessel 401, the pipe 416 is connected through the pipe 416a to switching ports of the third and fourth three-way valves 483, 484. If the third three-way valve 483 is driven to be ON in this state, the communication through the pipe 417 between the second airtight chamber 401b of the ventilation vessel 401 and the flow meter 491 is interrupted, and at the same time the first flow meter 491 is connected to the suction system 410 through the pipes 416 and 416a. If the fourth three-way valve 484 is driven to be ON under the condition that the second three-way valve 482 is in an OFF state, the connection through the pipe 418 between the suction system 410 and the third airtight chamber 401c of the ventilation vessel 401 is interrupted, and at the same time the second flow meter 492 is connected through the pipes 416a and 416 to the suction system 410.

According to the ventilation-characteristic measuring apparatus configured such that the pipe arrangement between the suction system 410 and the ventilation vessel 401 or the pipe arrangement between the suction system 410 and the first and second flow meters 491, 492 is selectively switched with use of the second, third and fourth three-way valves 482, 483 and 484, a measurement on ventilation (air flow rate ratio) and ventilation resistance of a cigarette C held in the ventilation vessel 401 is carried out as shown below.

Figure 17:
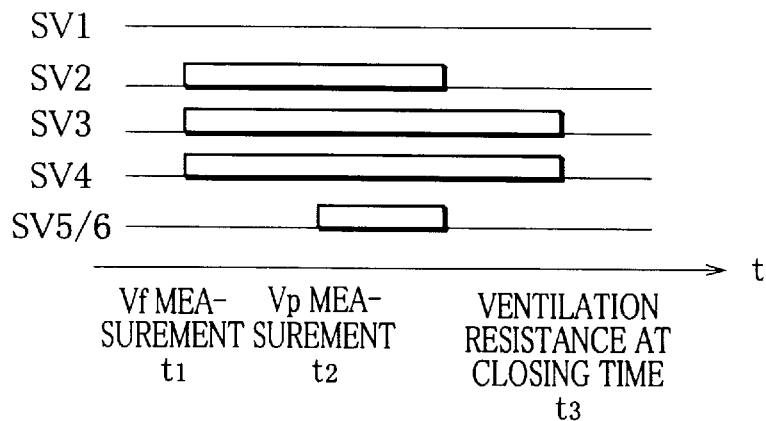
FIG. 17 is a view of switching control timings of three-way valves during the ventilation characteristic measurement on a cigarette effected with use of the ventilation-characteristic measuring apparatus shown in FIGS. 10 and 16.

For the ventilation resistance measurement on a cigarette C, the cigarette C is held in the ventilation vessel 401, and in this state, the suction system 410 is connected to the first airtight chamber 401a of the ventilation vessel 401 through the pipe 416 by causing the second three-way valve 482 to be ON while maintaining the first three-way valve 481 at an OFF state to thereby no standard test piece 415 is provided in the pipe 416, as shown in FIG. 17 showing ON and OFF timings of the three-way valves 481, 482, - - - , 486. Under this condition, the third and fourth three-way valves 483 and 484 are caused to be ON, so that the first and second flow meters 491 and 492 are connected through the pipes 417 and 418 to the second and third airtight chambers 401b and 401c of the ventilation vessel 401, respectively.

At first, the first airtight chamber 401a of the ventilation vessel 401 is evacuated by the suction system 410 at the air flow rate regulated by the critical nozzle 413 in a condition that the fifth and sixth three-way valves 485 and 486 are maintained at ON states, so that the pressure meter 493 is kept connected to the pressure difference pipe 419a of the first flow meter 491. Subsequently, in this state, a flow rate Vf of air flowing through the first flow meter 491, more specifically, the flow rate Vf of air flowing from an atmosphere opening port of the flow meter 491 to the cigarette C through the pipe 417, the second airtight chamber 401b and the filter section F of the cigarette is measured (timing of t1). Actually, the air flow rate Vf is measured by the pressure meter 493 as a pressure difference produced in the first flow meter 491.

Next, the fifth and sixth three-way valves 485 and 486 are caused to be in ON states, to thereby connect the pressure meter 493 to the pressure difference pipe 419b. In this state, the first airtight chamber 401a of the ventilation vessel 401 is evacuated by the suction system 410, and a flow rate Vp of air flowing through the second flow meter 492, i.e., the flow rate Vp of air entering from an atmosphere opening port of the flow meter 492 to the cigarette C through the pipe 418, the third airtight chamber 401c and the tobacco section T of the cigarette is measured (timing of t2).

Thereafter, the third three-way valve 483 is turned OFF to thereby interrupt the connection through the pipe 417 between the first flow meter 491 and the second airtight chamber 401b, and an output (ventilation resistance at the time of closing) of a manometer 420 is measured (timing of t3). In the control section 700 having an arithmetic function, a ventilation resistance at the releasing time and that at the closing time are determined from the air flow rates Vf and Vp, and makes an evaluation on qualities of the cigarette C.

A total flow rate of air passing through the cigarette C and also passing through the first airtight chamber 401a of the ventilation vessel 401 equals to a constant flow rate regulated by the critical nozzle 413. Thus, the ratio of a flow rate of air, entering into the cigarette through the filter section F of the cigarette, to the total flow rate is determined by Vf/17.5 and the ratio of a flow rate of air, entering into the cigarette through the shredded tobacco section T, to the total flow rate is determined by Vp/17.5. Based on these ratios, qualities of the cigarette C are evaluated.

Figure 18:
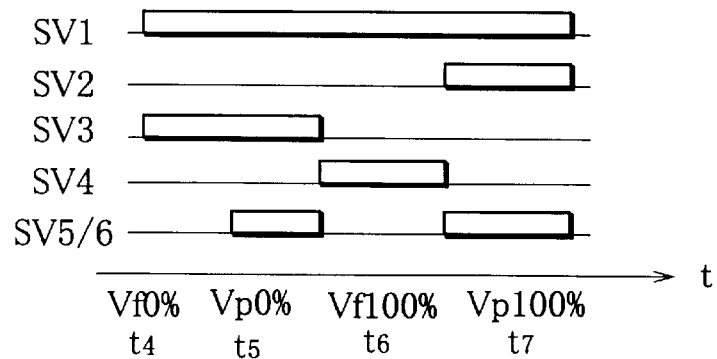
FIG. 18 is a view of switching control timings during the calibration of a flow meter effected with use of the ventilation-characteristic measuring apparatus shown in FIGS. 10 and 16.
Figure 19:
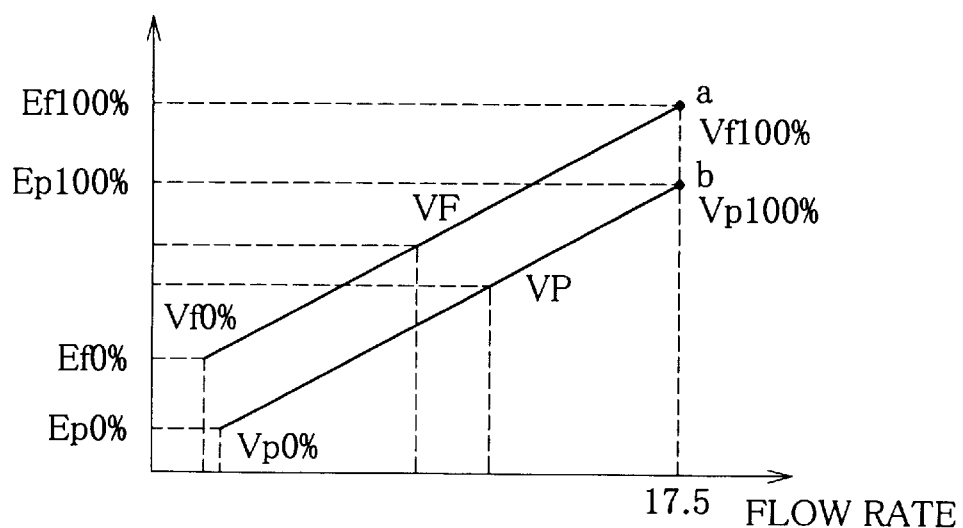
FIG. 19 is a view showing a calibration line used for calibration of a flow meter.

As described above, flow-rate measuring characteristics of the first and second flow meters 491, 492 and of the pressure meter 493 can be calibrated. In order to make a calibration of this measuring system, as shown in FIG. 18 showing on-off timings of the three-way valves 481, 482, - - - , 486, the first three-way valve 481 is caused to be ON to thereby interpose a standard test piece 415, having a predetermined standard ventilation resistance, between the suction system 410 and the measuring system.

In this state, the second three-way valve 482 is turned ON so as to connect the suction system 410 with the first airtight chamber 401a of the ventilation vessel 401. At this time, the third and fourth three-way valves 483, 484 are kept in OFF states, so that the second and third airtight chambers 401b, 401c of the ventilation vessel 401 are closed, whereby the first and second flow meters 491, 492 are disconnected from the suction system 410. Under this condition, the fifth and sixth three-way valves 485, 486 are kept in OFF states, to thereby connect the pressure meter 493 with the first flow meter 491. Then, a flow rate of air in a condition that no air enters into the second airtight chamber 401b through the first flow meter 491 is measured. In other words, a pressure (Vf 0%) at 0% flow rate generated when the flow meter 491 is closed is measured (timing of t4).

Next, the fifth and sixth three-way valves 485, 486 are turned ON with the fourth three-way valve 483 kept in the OFF state, to thereby connect the pressure meter 493 with the second flow meter 492. Then, a flow rate of air in a condition that no air enters into the third airtight chamber 401c through the second flow meter 492 is measured. In other words, a pressure (Vp 0%) at 0% flow rate generated when the flow meter 492 is closed is measured (timing of t5).

After the flow rates of air observed when the first and second flow meters 491, 492 are closed are measured, respectively, the second three-way valve 482 is turned OFF to thereby disconnect the suction system 410 from the first airtight chamber 401a of the ventilation vessel 401 and connect the suction system 410 with the pipes 417, 418 through the pipe 416a. Subsequently, the fourth three-way valve 484 is turned ON, to thereby connect the second flow meter 492 with the third airtight chamber 401c of the ventilation vessel 401 through the pipe 418 and interrupt the connection between the flow meter 492 and the suction system 410 through the pipes 416a, 416. Then, the third three-way valve 483 is turned OFF to connect the first flow meter 491 with the suction system 410 through the pipes 417, 416a and 416, and the fifth and sixth three-way valves 485, 486 are turned OFF to connect the pressure meter 493 with the first flow meter 491. Under this condition, only the first flow meter 491 is evacuated at a flow rate regulated by the critical nozzle 413 (timing of t6). Thus, air flows through the first flow meter 491 at a flow rate of 100%, and a pressure difference produced in the first flow meter 491 in this condition is measured by the pressure meter 493 (Vf 100%).

Next, the fourth three-way valve 484 is turned OFF and the third three-way valve 483 is turned ON, to thereby disconnect the first flow meter 491 from the suction system 410 and connect the suction system 410 with the second flow meter 492. Subsequently, the fifth and sixth three-way valves 485 and 486 are turned ON again, to thereby connect the pressure meter 493 with the second flow meter 492, whereby the second flow meter 492 alone is evacuated at a flow rate regulated by the critical nozzle 413 (timing of t7). As a consequence, there occurs a stream of air flowing through the second flow meter 492 at a flow rate of 100%, and a pressure difference produced in the second flow meter 492 in this condition is measured by the pressure meter 493 (Vp 100%). The above-mentioned flow rate measurements for the first and second flow meters 491, 492 disconnected from the ventilation vessel 401 are conducted prior to testing on cigarettes C or at intervals of a predetermined calibration cycle, for instance, independently of testing on cigarettes.

By measuring the pressures produced in the first and second flow meters 491, 492 attributable to the flow of air at a flow rate of 100% and the pressures produced therein when these flow meters are closed (at the time of 0% air flow rate), pressure difference outputs Ef100% and Ep100% observed at 100% air flow rate or observed when the flow meters 491, 492 are evacuated at the flow rate regulated by the critical nozzle 413 can be determined and pressure difference outputs Ef0% and Ep0% observed at 0% air flow rate or observed when the flow meters are closed can be measured. Whereupon, calibration characteristic lines VF and Vp connecting associated measured output values are determined in the control section 700 having arithmetic functions. By calibrating, based on the calibration lines, outputs E of the pressure meter 493 produced at the time of measuring the flow rates of air entering from the second and third airtight chambers 401b, 401c, the air flow rates Vf and Vp can be determined with accuracy.

According to the ventilation-characteristic measuring apparatus constructed as described above, the flow rate Vf of air entering from the second airtight chamber 401b of the ventilation vessel 401 thorough the filter section F of a cigarette and the flow rate Vp of air entering from the third airtight chamber 401c through the tobacco section T of a cigarette can be measured with ease and with accuracy, since an appropriate passage (pipe) through which a stream of air flows at a constant flow rate under suction produced by the suction system 410 can be selected by simply controlling the drive of the first through sixth three-way valves 481, 482, - - - , 486. In addition, 100% flow rate of air flowing through each of the first and second flow meters 491, 492 for measuring the flow rates Vp and Vf can be easily measured by connecting each flow meter directly with the suction system 410. This makes it possible to calibrate the measuring characteristics of the first and second flow meters 491, 492 with ease so as to compensate for changes in the measuring characteristics, whereby the air flow rate measurement can be always made accurately.

Flow-rate-dependent pressure produced in the first and second flow meters 491, 492 can be measured with use of a single pressure meter 493 by switching the fifth and sixth three-way valves 485, 486 in an interlocking manner to selectively connect the pressure meter 493 with the first or second flow meter 491 or 492. Thus, the single pressure meter 493 comprised of a high-priced minute pressure-difference sensor is effectively utilized, whereby costs for pressure measurement can be reduced, resulting in a reduction in overall costs of the ventilation-characteristic measuring apparatus, while enjoying a high response speed of the minute pressure-difference sensor.

If a measurement value obtained in the measurement on 100% flow rate or 0% flow rate at the closed state in respect of the first and second flow meters 491, 492 falls outside a predetermined allowed range, an alarm indicative of an abnormality of the measuring system may be delivered. By doing this, an erroneous measurement can be prevented in advance. The control of switching pipe arrangements based on the on-off control of the first through sixth three-way valves 481, 482, - - - , 486 can be executed with a logic which is reverse of that of the embodiment.

Figure 1:
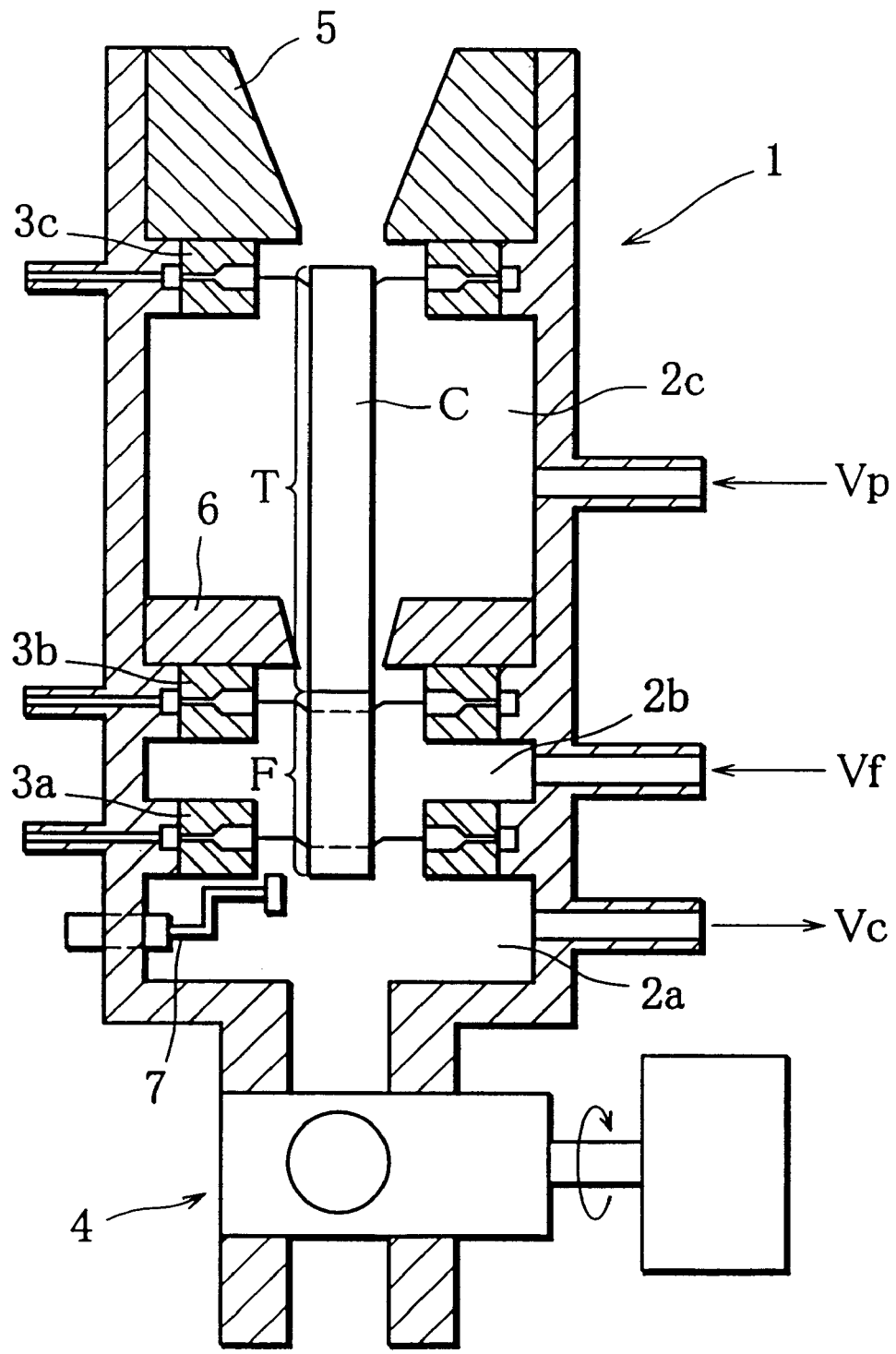
FIG. 1 is a schematic view showing a conventional ventilation apparatus.
Figure 2:
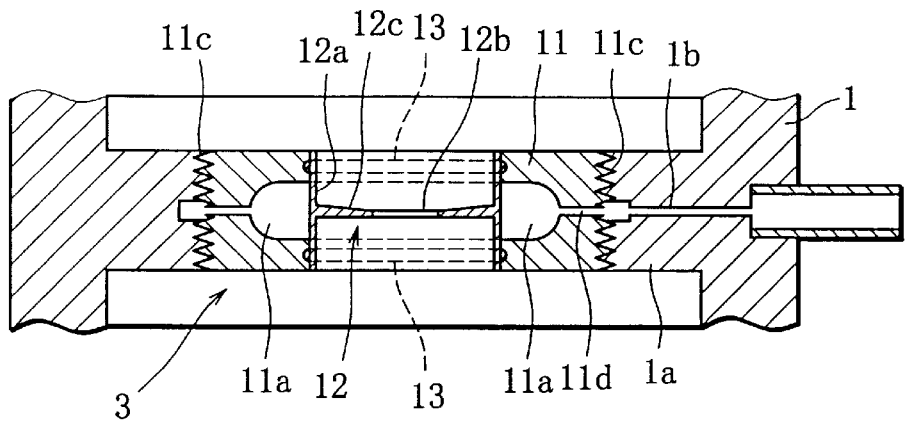
FIG. 2 is a schematic view showing a conventional test-piece supporting device.
Figure 3:
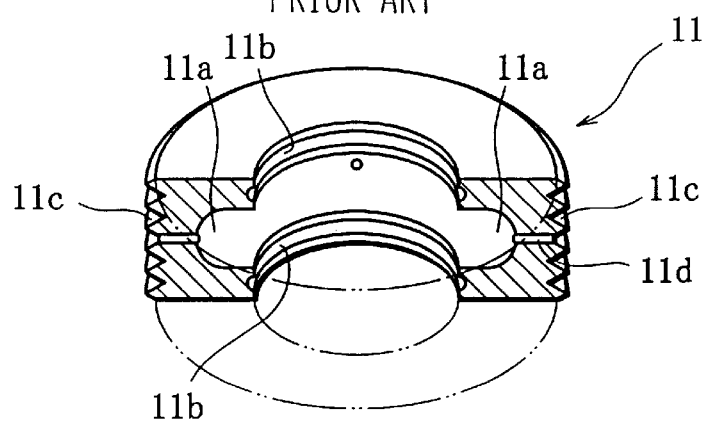
FIG. 3 is a view showing a holder of the test-piece supporting device shown in FIG. 2.
Figure 4:
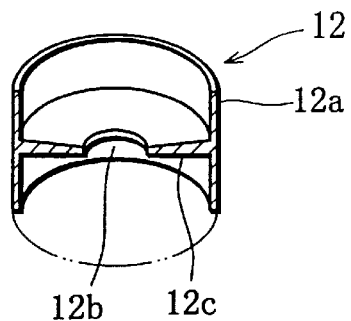
FIG. 4 is a view showing a test-piece holding member of the test-piece supporting device shown in FIG. 2.

The ventilation-characteristic measuring apparatus of this invention is not limited to the foregoing embodiment. For instance, a test-piece supporting apparatus 470 having a test-piece holding member 12 shown in FIG. 4 which is attached to the inner periphery of the holder 471 through O-rings, instead of the test-piece holding member 472 shown in FIG. 12 through FIG. 16, may be accommodated in each of the cylindrical containers 430, 440, 450. Further, the ventilation vessel may be configured in such a manner that the second cylindrical container 440 is fitted on the outer periphery of the first cylindrical container 430 and that the third cylindrical container 450 is fitted on the outer periphery of the second cylindrical container 440.

In the case of testing a so-called double-cut cigarette C provided with no filter section, or testing a filter rod having a predetermined length and adapted to be attached to a cigarette, the holding of such a cigarette C or a filter rod by means of the test-piece supporting device 470 attached to the second cylindrical container 440 may be released.

Annular grooves for receiving O-rings 475 may be formed in an outer peripheral face of the holder 471 so as to regulate the mounting position of the O-rings, as long as an airtight chamber can be defined between a central part of the outer peripheral face of the holder 471 and an inner peripheral face of an associated cylindrical container by the upper and lower O-rings 475 attached to the outer peripheral face of the holder 471.

Length/hardness measuring section

When a stopper 435 moves to its receding position in the ventilation vessel after the ventilation characteristic measurement by the ventilation-characteristic measuring section 400 is finished, a cigarette C is ejected, due to its own weight, from the ventilation-characteristic measuring section 400 to a length/hardness measuring section 500 disposed below the measuring section 400.

Figure 20:
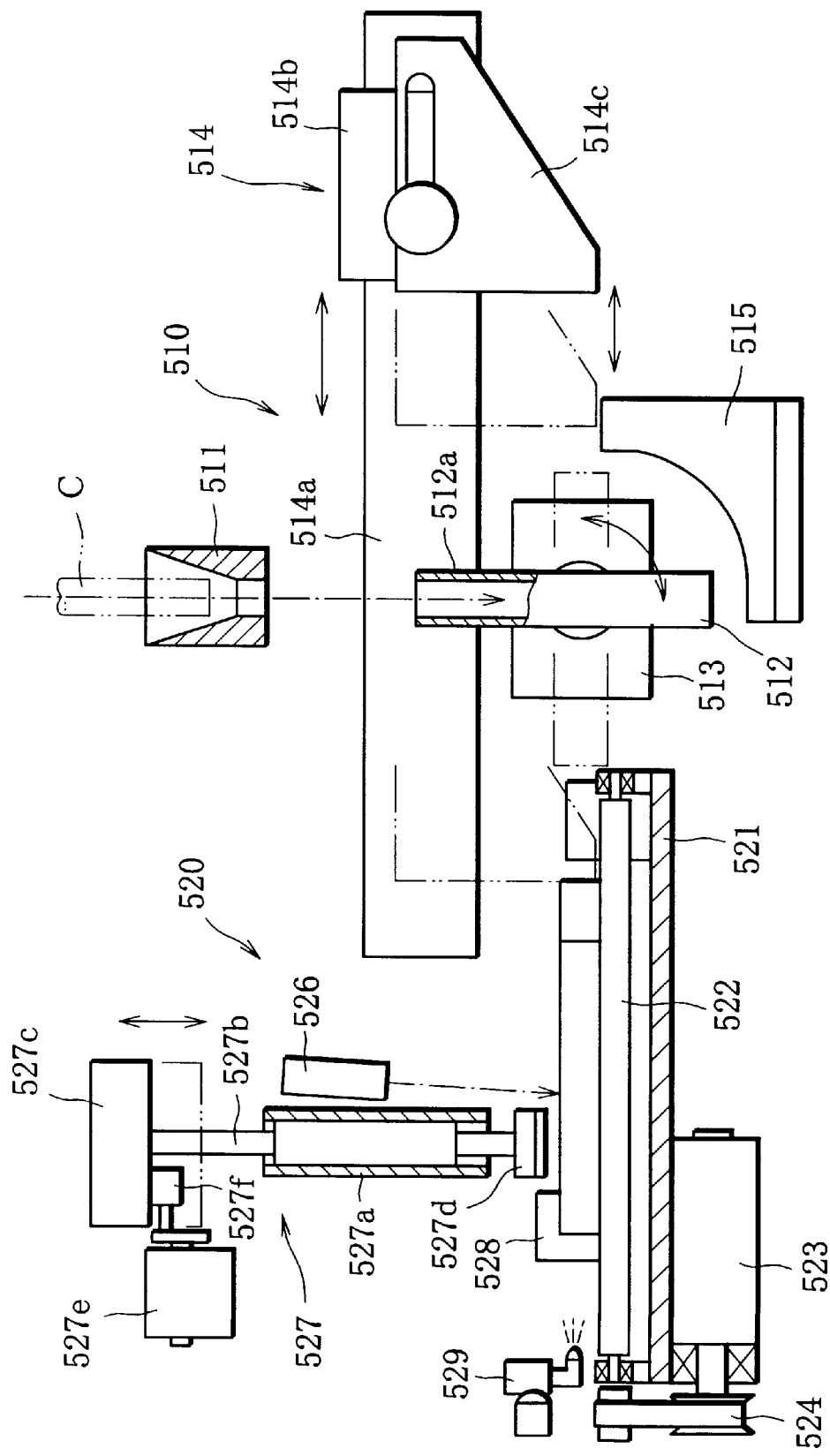
FIG. 20 is a view showing a length/hardness measuring section shown in FIGS. 6 and 7.

As shown in FIGS. 6, 7 and 20, the length/hardness measuring section 500 comprises a transferring mechanism 510 and a measuring unit 520 for a cigarette C. The transferring mechanism 510 is comprised of a guide 511 for guiding a cigarette C falling perpendicularly from the ventilation-characteristic measuring section located above the transferring mechanism, a cylindrical rotary holder 512 for receiving the cigarette C introduced thereinto through the guide 511, a holder rotating mechanism 513 for rotating the rotary holder 512, having an axial center thereof supported by the holder rotating mechanism, to change the direction of the rotary holder to thereby change the direction of the cigarette C between a vertical position and a horizontal position, and a pusher mechanism 514 for pressing one end face of the cigarette C having the horizontal position, to thereby transfer the cigarette C from the holder 512 to the measuring unit 520.

The guide 511 serves to introduce the cigarette C ejected from the ventilation-characteristic measuring section 400 into the holder 512 disposed vertically. The holder 512 is comprised of a cylindrical body having a peripheral wall thereof axially formed with a groove (slit) 512 for permitting a pressing piece (pusher), mentioned later, of the pusher mechanism 514 to pass through the holder 512. The holder 512 has an inner diameter which is slightly larger than the maximum diameter among diameters of cigarettes C, so that a respective cigarette C is smoothly inserted into and held by the holder 512.

With the action of the rotating mechanism 513, the holder 512 is rotated and directionally changed from a vertical position to a horizontal position, to thereby maintain the cigarette C held therein in a horizontal position. A block 515 has a circular arc face thereof disposed along the locus of rotation of the holder 512 and permits the cigarette C introduced into the holder 512 to be in contact at its one end face (outer end face of the filter section) with the block 515, to thereby regulate the position in which the cigarette C is held by the holder 512 and to prevent the cigarette C from dropping from the holder 512 during the rotation of the holder.

The pusher mechanism 514 further comprises a movable carrier 514b movable along a guide rail 514a, and a pressing piece (pusher) 514c comprised of a plate attached to the movable carrier 514b and adjustable in attached position. The pusher mechanism 514 is driven in a state that the holder 512 is in a horizontal position, so that the movable carrier 514b moves horizontally along the guide rail 514a. During the movement of the movable carrier, the pressing piece 514c passes through the holder 512 through the groove 512a and presses one end face of the cigarette C held in the holder 512, to thereby transfer the cigarette C from the holder 512 to the measuring unit 520. As mentioned later, the pressing piece 514c serves to regulate the position of one end of the cigarette C having been transferred onto the measuring unit 520.

The measuring unit 520 comprises two revolving rollers 522 which are disposed in parallel to a framework 521 and which constitute a measuring stage. These rollers 522 are disposed in alignment with the holder 512 having a horizontal position, with their one end portions located at locations close to the holder 512. The rollers 522 permit a cigarette C transferred horizontally from the holder 512 to be slide thereon in a condition that the direction of the cigarette is kept unchanged, to thereby axially guide the cigarette which is then positioned in place for length/hardness measurement. The rollers 522 are rotatively driven, where required, e.g., through a belt mechanism 524 by a motor 523 mounted on a bottom face of the framework 521.

In relation to the cigarette length measurement, a photosensor 528 is disposed laterally of the rollers 522 and an optical path of the photosensor extends to cross another end portion of the cigarette C placed on the rollers 522. The photosensor 528 is comprised of a transmitter and a receiver, disposed on the both sides of the rollers 522, for transmitting and receiving therebetween a slit light beam having a predetermined beam width. The position of another end (distal end) of a cigarette C is measured based on a width for which the slit light is blocked by the cigarette C, i.e., based on a slit light width detected by the receiver among the predetermined slit light width. Then, the length of the cigarette C is measured from the measured position of the distal end of the cigarette C and the position of one end of the cigarette C regulated by the pressing piece 514c.

Although cigarettes C are different in length and thickness depending on cigarette brands, the apparatus of this embodiment is arranged to carry out the length measurement in a state that a cigarette is placed on a pair of rollers 522, so as to remove an affection of difference in cigarette thickness to the measurement. Further, by adjusting the mounting position of the pressing piece 514c onto the movable carrier 514b, a regulated position (reference point) of one end of a cigarette C on the rollers 522 is changed in accordance with the length of the cigarette C, to thereby make it possible to position another end portion of the cigarette C within a sensing region of the slit light generated by the photosensor 528, irrespective of a standard cigarette length varying depending on cigarette brand.

More specifically, for the length measurement on test pieces, a reference point is set in advance in such a manner that part of the laser light beam is blocked by a distal end portion of a standard gauge having a known length. In the case of a length measurement on test pieces having a standard length of 85.0 mm, for instance, a standard gauge having a length L0 (=85.0 mm) is placed on the rollers 522, and the mounting position of the pressing piece 514c onto the movable carrier 514b is adjusted so that the distal end of the standard gauge is located at the center of the laser light beam. If the transmitter and the receiver of the photosensor 528 are configured by laser sensors of a type where an output of the receiver varies from 1 volt generated when the laser beam is fully blocked to 5 volts generated when it is not blocked at all, the mounting position is adjusted in such a manner that the output voltage of the receiver becomes equal to 3 volts.

The deviation of the length of a test piece from that of the standard gauge, or the length L of the test piece, is measured based on the difference between the outputs of the receiver observed when part of the laser light beam is blocked by the standard gauge and when it is blocked by the test piece. That is, the length of the test piece is determined in accordance with the formula of $L=L0+(E-3.00)$, where E represents the output voltage of the receiver at the time of length measurement on the test piece.

In relation to a cigarette hardness measurement, a pressurizing mechanism 527 is disposed above the rollers 522. The pressurizing mechanism 527 comprises a rod 527b supported by a cylinder 527a so as to be vertically movable, a loading plate 527c, attached to an upper end of the rod 527b, for applying a predetermined downward load to the rod 527b, and a pressurizing member 527d, mounted to a lower end of the rod 527d, for applying the downward load to a peripheral face of a cigarette C placed on the rollers 522, to thereby press the cigarette peripheral face from above. The vertical motion of the rod 527b (or the pressurizing member 527d) is controlled by an eccentric roller 527f which is eccentrically mounted to a rotary shaft of a motor 527e and which is adapted to abut against a lower face of the loading plate 527c and lift the loading plate 527c.

In relation to the hardness measurement, the measuring unit 520 comprises a photosensor which is comprised of a transmitter (not shown), disposed laterally of the rollers 522, for projecting a laser light beam, and a receiver, disposed on the opposite side of the rollers so as to face the transmitter, for receiving a laser beam from the transmitter and for generating an output voltage which varies depending on an amount of received of light. In this embodiment, the above-mentioned photosensor is constituted by the photosensor 528 explained above. When a cigarette C is placed on the rollers 522, part of the laser beam is blocked by the cigarette. If the loading member 527d is brought in contact with the cigarette, the laser beam is fully blocked by the loading member and the cigarette. At this time, the receiver generates a prescribed voltage.

Figure 21:
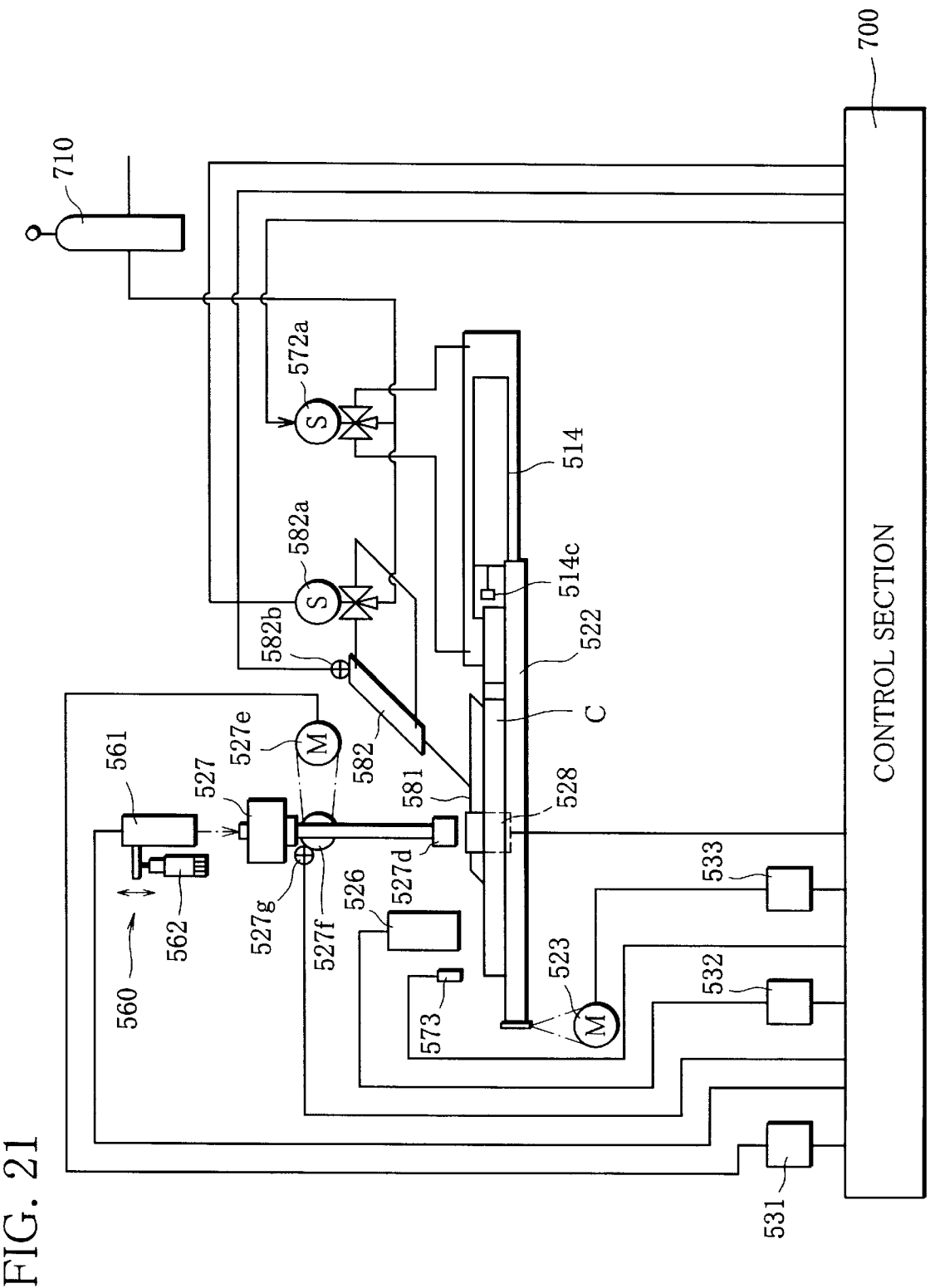
FIG. 21 is a schematic diagram showing a control system for the length/hardness measuring section.

The measuring unit 520 further comprises a displacement detecting section 560 for detecting the position of the pressurizing member 527d (FIG. 21). The displacement detecting section 560 is comprised of a laser displacement gauge 561 for projecting a laser beam toward an upper end face of the loading plate 527c of the pressurizing mechanism and for receiving a reflected light beam from the loading plate, to generate a voltage indicative of a distance, determined by triangulation, to the upper end face of the loading plate, and an adjuster 562 for adjusting the position of the displacement gauge 561. As the displacement gauge 561, an MQ laser analog sensor of LA40 type, manufactured by Matsushita Electric Works, Ltd., or the like may be employed.

Prior to the hardness measurement with use of the above-mentioned measuring unit 520, a criterion adjustment is carried out. In the criterion adjustment, a standard gauge (not shown) which is rigid and has a known diameter is placed on the rollers 522, and the position of the laser displacement gauge 561 is adjusted by the adjuster 562 in such a manner that the output voltage of the displacement gauge 561 becomes equal to a prescribed value, e.g., 0 volt, in a condition that the pressurizing member 527d in a free state is brought in contact with the standard gauge.

Upon an actual hardness measurement, the pressing piece 514c is moved forward from the length measurement position by a predetermined distance varying depending on the brand of a cigarette C, and pressurized air is injected from the air nozzle device 529 so that the position of one end of the cigarette C is reliably regulated by the pressing piece 514c, whereby the position of the cigarette C is re-adjusted. As a consequence, a center part of shredded tobacco portion T of the cigarette C can be easily positioned at a pressurizing position to which the pressurizing member 527d of the pressurizing mechanism 527 is positioned. Thus, the hardness measurement can be carried out by pressurizing substantially the center part of the shredded tobacco portion T of the cigarette T by means of the pressurizing member 527d. In the meantime, a directionality is produced in shredded tobacco in a cigarette during the processes, constituting part of cigarette manufacturing processes, of wrapping shredded tobacco by a paper and of pasting edge portions of the wrapping paper. As a result of this directionality of shredded tobacco, a hardness measurement result may vary depending on whether a pressure for cigarette hardness measurement is applied to a lap portion of the wrapping paper or a circumferential portion other than the lap portion, causing a measurement error. To obviate this, in the present embodiment, a cigarette C is rotated on the rollers 522 by rotatively driving the rollers 522 by the motor 523, and the cigarette rotation is caused to stop when a lap portion (a pasted portion of a paper by which shredded tobacco is wrapped) is detected by the photosensor 526, to thereby always apply a pressure for hardness measurement is always applied to the same cigarette portion. The lap portion is detected by the photosensor 526 in the form of a change in an amount of reflected light. The photosensor 526 projects light onto a peripheral face of a cigarette C placed on the rollers 522 and detects reflected light therefrom.

As a photosensor (mark sensor) 526, a supper analog sensor RS-120HF-5G-SAS manufactured by Sankusu Corporation in Japan, for instance, may be used.

In the hardness measurement, both of an output voltage of the displacement gauge 561 generated when the pressurizing member 527h is in contact with a cigarette and an output voltage of the displacement gauge generated when a predetermined load is applied to the cigarette by the pressurizing mechanism 527 are detected. Subsequently, a cigarette diameter D1 observed when the pressurizing member is in contact with the cigarette is determined on the basis of the difference between output voltages respectively generated when the pressurizing member is in contact with the cigarette and when it is in contact with the standard gauge. Further, a cigarette diameter D2 at the time of applying a load to the cigarette is determined on the basis of the difference between output voltages respectively generated when a load is applied to the cigarette and when the pressurizing member is in contact with the standard gauge. Then, an amount of deformation E (%) of the cigarette caused by the application of load and indicative of the cigarette hardness is determined in accordance with the formula of $\epsilon = 100(D1-D2)/D1$.

Control system for length/hardness measuring section

As shown in FIG. 21, the holder rotating mechanism 513 and the pusher mechanism 514 of the transferring mechanism 510, the motor 523 of the measuring unit 520 for the revolving rollers, and the motor 527e of the pressurizing mechanism 527 are operated under the control of the control section 700. In FIG. 21, a control system associated with the holder rotating mechanism 513 is omitted. The control system for the holder rotating mechanism 513 may be constituted in a similar manner as a corresponding part of the control system shown in FIG. 9.

Connected to the control section 700 are a controller 531 for controlling the drive of the motor 527e of the pressurizing mechanism 527, a controller 532 for detecting an output voltage of the mark sensor 526 and for supplying the control section 700 with a lap portion detecting signal when the controller detects a change in output voltage indicative of a lap portion of a test piece, and a controller 533 for controlling the drive of the motor 523 for the revolving rollers.

Further connected to the control section 700 are a solenoid valve 572a, disposed in a pipe which connects the pusher mechanism 514 with a pressurized-air source 710, for changing the direction of pressurized air supply to the pusher mechanism 514, and a solenoid valve 582a, disposed in a pipe which connects an ejection pusher cylinder 582 with the pressurized-air source 710, for changing the direction of pressurized air supply to the ejection pusher cylinder 582.

The pusher mechanism 514 is caused to have an ON or OFF state in response to the switching action of the solenoid valve 572a. The positioning mechanism causes, in an ON state, the pusher 514c to move to the left side in FIG. 20, whereas it causes the pusher 514c to the opposite side in an OFF state. The ejecting pusher cylinder 582 is caused to have an ON or OFF state in response to the switching action of the solenoid valve 582a. This cylinder operates, in an ON state, to cause the ejection pusher 581 to move in the direction close to the revolving rollers 522, and operates, in an OFF state, to cause the pusher 581 to move in the direction away from the rollers 522. An ejecting pusher switch 582b is turned on when the ejecting pusher 581 is retreated in the ejecting pusher cylinder 582, whereas it is turned off as the test piece is ejected by the ejecting pusher 581.

In FIG. 21, reference numeral 527g denotes an eccentric roller switch which is turned on when the rod 527b of the pressurizing mechanism 527 is at its upper receding position.

In relation to the length/hardness measurement, the control section 700 drives the pusher mechanism 514 until a positioning sensor 573 is turned on in a condition that the ejecting pusher switch 582b and the eccentric roller switch 527g are in their ON positions, to thereby cause the pusher 514c to move up to its length measurement position. Whereupon, the length measurement on the test piece is carried out.

Upon completion of the length measurement, the pusher 514c is caused to move forward from the length measurement position by a predetermined distance, to thereby position the same at a hardness measurement position. Under this state, the air nozzle device 529 is driven so as to cause the test piece to abut against the pusher 514c, to thereby position the test piece at the hardness measurement position. Subsequently, the motor 523 for the revolving rollers is driven, so that the test piece rotates on the revolving rollers 522. When a lap portion detecting signal is delivered from a mark sensor controller 532 in this condition, the motor 523 is caused to stop.

Next, the control section 700 drives the motor 527e of the pressurizing mechanism 527 through the controller 531, and monitors the output voltage of the photosensor 528. When detecting that the pressurizing member 527d is brought in contact with the test piece, the control section causes the motor 527e to stop and reads out the output voltage (position data) of the laser displacement gauge 561, the read output voltage being stored in a memory. Subsequently, the motor 527e of the pressurizing mechanism 527 is driven. After a predetermined load is applied to the test piece over a predetermined period of time, the control section reads out the output voltage of the laser displacement gauge 561 and stores the same in the memory.

When the eccentric roller switch 527g is turned on as the motor 527e is driven, the control section causes the motor 527e to stop, and sets the ejecting pusher cylinder 582 in an ON state for a predetermined time period, so that the test piece on the revolving rollers 522 is ejected toward the ejection box 800 (FIG. 6).

When the test piece ejection is finished, the control section reads out pieces of position data from the memory, and calculates an amount of deformation of the test piece, indicative of its hardness. Whereupon, the hardness measurement is finished.

Figure 24:
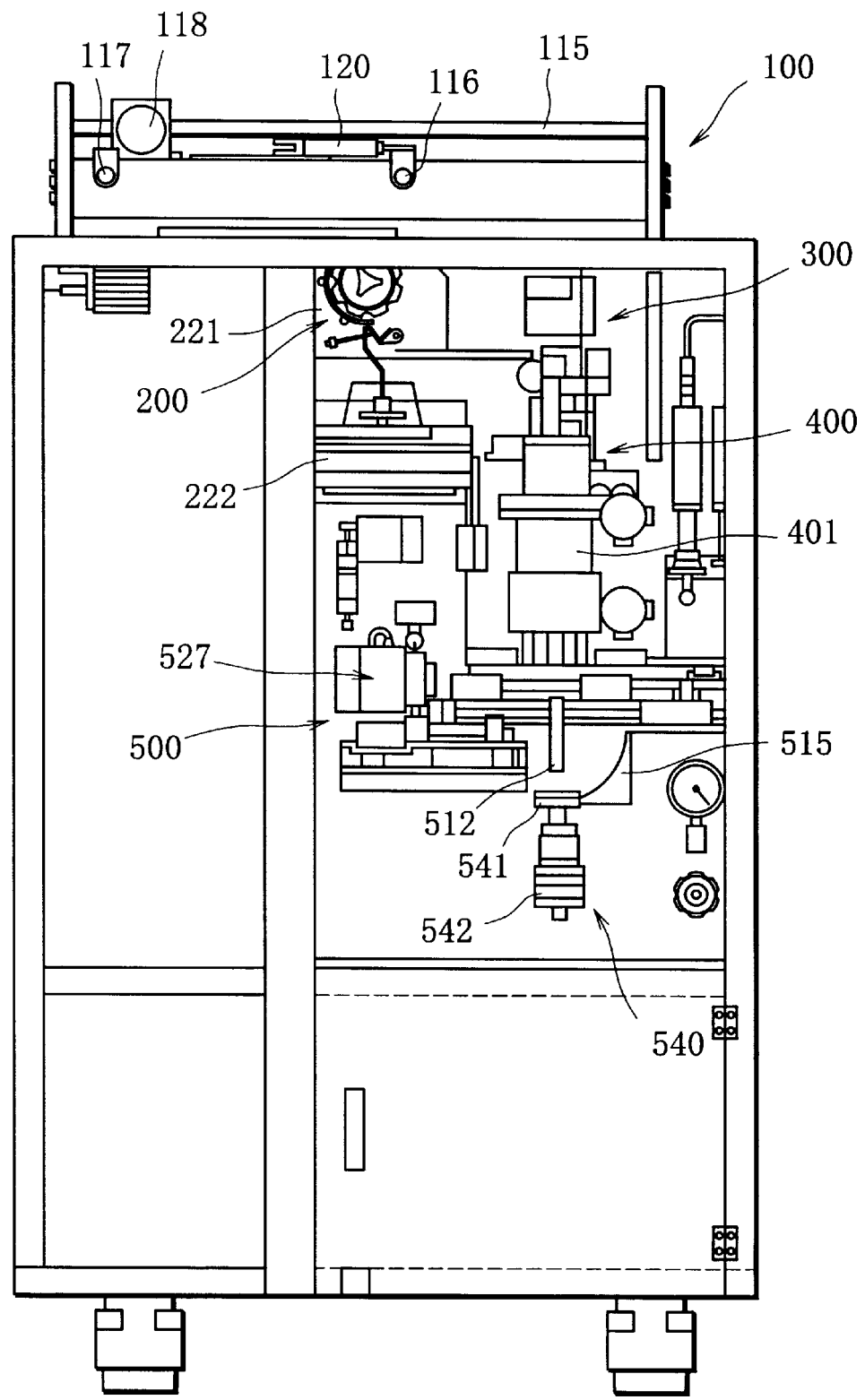
FIG. 24 is a schematic front view showing a different cigarette testing apparatus equipped with a ventilation-characteristic measuring apparatus according to the present invention.
Figure 25:
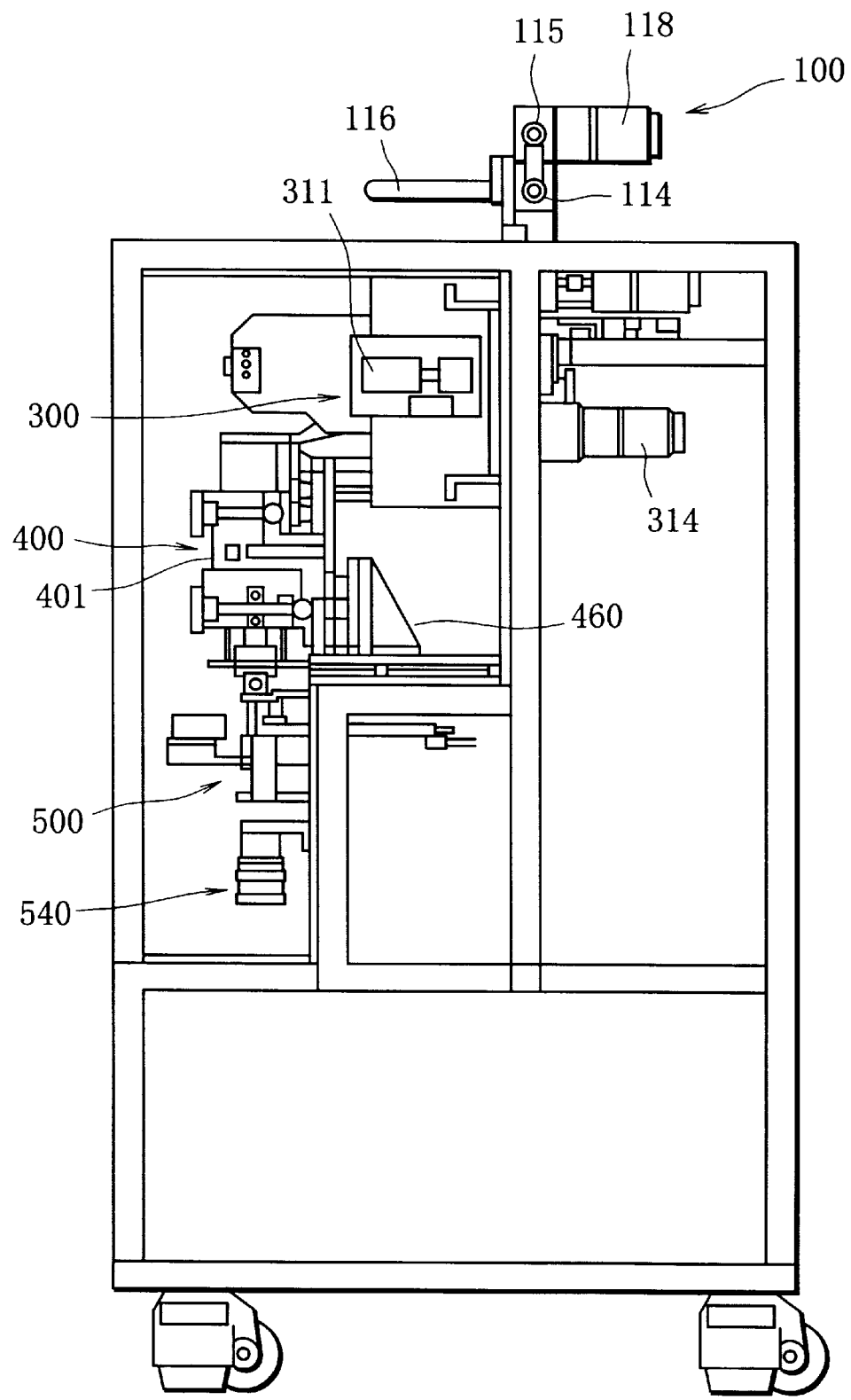
FIG. 25 is a schematic side view of the cigarette testing apparatus shown in FIG. 24.

With reference to FIGS. 24 and 25, a cigarette testing apparatus different from the apparatus shown in FIGS. 6 and 7 will be explained hereinbelow.

As compared to the apparatus shown in FIGS. 6 and 7, the cigarette testing apparatus shown in FIGS. 24 and 25 is mainly different in that part of the length/hardness measuring section 500 which relates to the length measurement, and has a cigarette supplying section 100, a weight measuring section 200, a circumference measuring section 300 and a ventilation characteristic measuring section 400 which are substantially the same as those shown in FIGS. 6 and 7.

As shown in FIGS. 24 and 25, the length/hardness measuring section 500 of the cigarette testing apparatus comprises, in relation to the length measurement, a transmitter (not shown) for projecting a laser beam, a receiver (not shown) for receiving the laser beam from the transmitter and for generating a voltage which varies in accordance with an amount of receiving of light, and a micrometer head 540 disposed below the rotary holder 512. The micrometer head 540 includes a micro head 541 on which a test piece C inserted in the holder 512 is placed when the holder 512 is in a vertical position, and an adjusting knob 542 for a fine adjustment of a vertical position of the micro head 541.

Prior to the length measurement on a test piece C, a reference point of the micro head 541 is set in advance in such a manner that the laser beam is partly blocked by a distal end portion of a standard gauge (not shown) having a known length. In an actual length measurement, a deviation of the length of a test piece C from that of the standard gauge, indicative of the length of the test piece, is measured based on the difference between a receiver output voltage observed when the laser beam is partly blocked by the standard gauge and that observed when it is blocked by the test piece C. After the length measurement on the test piece C is finished, the test piece C is transferred by the pusher mechanism 514 toward the two revolving rollers 522 constituting a measuring stage in which a hardness measurement on the test piece C is carried out by use of the pressing mechanism 527.

As described in the above, a ventilation-characteristic measuring apparatus of this invention is adapted to carry out a measurement on ventilation characteristics of rod-shaped test pieces of various specifications with use of a simplified arrangement, and is applicable to a cigarette testing apparatus other than the cigarette testing apparatus according to the aforementioned embodiment. That is, the cigarette supplying section, circumference measuring section and length/hardness measuring section of a cigarette testing apparatus to which a ventilation-characteristic measuring section of the present invention is mounted are not limited to those described in the preferred embodiment. Further, it is not inevitably necessary to provide all of the cigarette supplying section, circumference measuring section and length/hardness measuring section in a cigarette testing apparatus adapted to be equipped with a ventilation-characteristic measuring section of this invention. Moreover, a ventilation-characteristic measuring apparatus of this invention may be employed singly, and is applicable to a ventilation characteristic measurement on test pieces other than cigarettes. A ventilation-characteristic measuring apparatus may be modified in various manners as already explained in the above.

What is claimed is:

1. A ventilation-characteristic measuring apparatus, comprising:
   a first cylindrical container having an outer end formed with an opening which permits a test piece to pass therethrough and which is selectively hermetically closed;
   a second cylindrical container disposed coaxially with said first cylindrical container and hermetically detachably fitted to said first cylindrical container;
   a third cylindrical container having an outer end which is formed with an opening which permits the test piece to pass therethrough and which is disposed coaxially with said first and second cylindrical containers, said third cylindrical container being disposed on a side away from said first cylindrical container with respect to said second cylindrical container in an axial direction of said ventilation-characteristic measuring apparatus and being hermetically detachably fitted to said second cylindrical container, said third cylindrical container cooperating with said first and second cylindrical containers to form a ventilation vessel;
   a moving apparatus for axially moving said third cylindrical container; and
   first, second and third test-piece supporting devices, detachably mounted to inner peripheral faces of said first, second and third cylindrical containers, respectively, for holding the test piece.

2. The ventilation-characteristic measuring apparatus according to claim 1, wherein said first, second and third cylindrical containers are configured to be disposed in a vertical position, so that said second cylindrical container is fitted to said first cylindrical container from above said first cylindrical container and that said third cylindrical container is fitted to said second cylindrical container from above said second cylindrical container.

3. The ventilation-characteristic measuring apparatus according to claim 1, wherein each of said first, second and third cylindrical containers is formed into a circular cylindrical container which is an annulus ring in traverse section.

4. The ventilation-characteristic measuring apparatus according to claim 1, wherein said first, second and third cylindrical containers are configured such that said second cylindrical container is fitted into said first cylindrical container and said third cylindrical container is fitted into said second cylindrical container.

5. The ventilation-characteristic measuring apparatus according to claim 4, wherein said second cylindrical container has a flange which is adapted to abut against an end face of said first cylindrical container on a side close to said second cylindrical container, and wherein said ventilation-characteristic measuring apparatus further includes a spacer which is mounted between the flange and an end face of said first cylindrical container.

6. The ventilation-characteristic measuring apparatus according to claim 1, further comprising:

a rod-shaped member holder, disposed at a location outside said ventilation vessel, for holding a positioning rod-shaped member in parallel to an axis of said ventilation vessel, wherein said moving apparatus includes a movable member to which said third cylindrical container is mounted, and a guide member movable in unison with the movable member and adapted to abut against one end of the positioning rod-shaped member held by the rod-shaped member holder.

7. The ventilation-characteristic measuring apparatus according to claim 1, wherein each of said first, second and third test-piece supporting devices comprises a ring-shaped holder having an inner peripheral face on which a test-piece holding member for detachably holding the test piece is held, and a pair of ring-shaped seal members mounted on an outer peripheral face of the ring-shaped holder at locations on axially opposite sides of the outer peripheral face, and wherein the ring-shaped holder is fitted on an inner peripheral face of a corresponding one of said first, second and third cylindrical containers.

8. The ventilation-characteristic measuring apparatus according to claim 1, wherein each of said first, second and third test-piece supporting devices comprises a ring-shaped holder detachably mounted to an inner peripheral face of a corresponding one of said first, second and third cylindrical containers, and a test-piece holding member made of an elastic material and formed with a test-piece supporting hole which permits the test piece to pass therethrough, said ring-shaped holder is formed at its inner peripheral face with a recess extending along the whole circumference thereof and is formed with a communication hole having opposite ends thereof opening to the recess and an outer peripheral face of the ring-shaped holder, respectively, said test-piece holding member comprises a tubular portion mounted to the inner peripheral face of the ring-shaped holder and closing an open face of the recess, and an annular flange radially inwardly projecting from the inner peripheral face of the tubular portion, said annular flange having its inner peripheral edge which defines the test-piece supporting hole, and each of said test-piece supporting devices further includes a pair of ring-shaped seal members which are mounted on opposite axial end sides of the outer peripheral face of the ring-shaped holder, respectively, the pair of ring-shaped seal members providing a seal between the ring-shaped holder and the inner peripheral face of the corresponding one cylindrical container, and forming a space, communicating with the communication hole, between the outer peripheral face of the ring-shaped holder and the inner peripheral face of the corresponding one cylindrical container.

9. The ventilation-characteristic measuring apparatus according to claim 8, wherein said holder is provided at its outer peripheral face with a position-regulating portion for regulating positions at which the pair of ring-shaped seal members are mounted.

10. The ventilation-characteristic measuring apparatus according to claim 8, wherein said test-piece holding member is provided at axially opposite ends of the tubular portion with a pair of jaw portions between which the holder is sandwiched, whereby the test-piece holding member is mounted to the holder.

11. The ventilation-characteristic measuring apparatus according to claim 10, wherein said holder comprises a pair of pressers fixed to axially opposite faces of the holder, respectively, through the jaw portions of the test-piece holding member mounted to the holder.

12. The ventilation-characteristic measuring apparatus according to claim 11, wherein said presser fixed to an axially outer face of the holder is formed into an annular shape and has its inner peripheral edge portion which is formed into a truncated conical face through which the test piece is introduced into the test-piece supporting hole of the test-piece holding member.

13. The ventilation-characteristic measuring apparatus according to claim 1, further comprising:

a suction apparatus, connected through a first pipe to a first airtight chamber defined by said ventilation vessel and said first test-piece supporting device, for evacuating the first airtight chamber at a flow rate regulated by a critical nozzle;

a first flow meter, disposed in a second pipe connected to a second airtight chamber which is defined by said ventilation vessel and said first and second test-piece supporting devices and which opens to an atmospheric air, for generating a pressure corresponding to a flow rate of air entering into the second airtight chamber through the second pipe as the first airtight chamber is evacuated;

a second flow meter, disposed in a third pipe which is connected to a third airtight chamber defined by said ventilation vessel and said second and third test-piece supporting devices, for generating a pressure corresponding to a flow rate of air entering the third airtight chamber through the third pipe;

a pressure meter, connected to said first and second flow meters through a fourth pipe, for measuring pressures generated in the first and second flow meters;

passage changeover valves, disposed in the first, second and third pipes, respectively, for selectively connecting said suction apparatus with said first or second flow meter; and a calibration apparatus for calibrating flow rate measuring characteristics of said first and second flow meters based on pressures measured by the pressure meter as the first and second flow meters are evacuated by said suction apparatus.

14. The ventilation-characteristic measuring apparatus according to claim 13, wherein each of said first and second flow meters generates a pressure difference between inlet and outlet ports thereof, the pressure difference varying in dependence on the flow rate of air flowing through the flow meter, and said pressure meter is comprised of a pressure difference sensor, and said ventilation-characteristic measuring apparatus further comprises first and second pressure-difference pipes extending between the inlet and outlet ports of the first and second flow meters and constituting the fourth pipe, and pressure changeover valves, respectively disposed in the first and second pressure-difference pipes, for selectively connecting the pressure meter to the first or second pressure-difference pipe.

15. The ventilation-characteristic measuring apparatus according to claim 13, wherein said calibration apparatus determines, as a pressure at 100% flow rate, the pressure measured by the pressure meter when the interior of each of said first and second flow meters is evacuated by said suction apparatus, determines, as a pressure at 0% flow rate, the pressure measured by the pressure meter when each of the flow meters is not evacuated by said suction apparatus, determines a calibration line in relation to the pressure and the flow rate in the flow meter, and calibrates the flow rate measuring characteristic in accordance with the calibration line.

\* \* \* \* \*

UNITED STATES PATENT AND TRADEMARK OFFICE
CERTIFICATE OF CORRECTION

PATENT NO. : 6,134,948
DATED : October 24, 2000
INVENTOR(S) : Seiji FUCHIGAMI et al.

It is certified that error appears in the above-identified patent and that said Letters Patent is hereby corrected as shown below:

Please insert section [30] as follows:

-- [30]    Foreign Application Priority Data

July 22, 1998 [JP] Japan ....................... 10-206905
July 22, 1998 [JP] Japan ....................... 10-206908
July 22, 1998 [JP] Japan ....................... 10-206909 --

Signed and Sealed this

First Day of May, 2001

Attest:

NICHOLAS P. GODICI

*Attesting Officer*            *Acting Director of the United States Patent and Trademark Office*